(12) United States Patent
Tomita et al.

(10) Patent No.: US 7,988,882 B2
(45) Date of Patent: Aug. 2, 2011

(54) POLYMERIZABLE LIQUID CRYSTAL COMPOUND, PHASE DIFFERENCE FILM AND LIQUID CRYSTAL DISPLAY USING THE SAME

(75) Inventors: Hidetoshi Tomita, Minami-Ashigara (JP); Michitaka Matsuumi, Minami-Ashigara (JP); Yasuhiro Aiki, Minami-Ashigara (JP); Ichiro Amimori, Minami-Ashigara (JP); Hidetoshi Watanabe, Minami-Ashigara (JP); Hideki Kaneiwa, Minami-Ashigara (JP)

(73) Assignee: Fujifilm Corporation, Tokyo (JP)

( * ) Notice: Subject to any disclaimer, the term of this patent is extended or adjusted under 35 U.S.C. 154(b) by 122 days.

(21) Appl. No.: 12/443,661

(22) PCT Filed: Nov. 21, 2007

(86) PCT No.: PCT/JP2007/072995
§ 371 (c)(1),
(2), (4) Date: Mar. 30, 2009

(87) PCT Pub. No.: WO2008/062900
PCT Pub. Date: May 29, 2008

(65) Prior Publication Data
US 2010/0047478 A1 Feb. 25, 2010

(30) Foreign Application Priority Data
Nov. 21, 2006 (JP) .................... 2006-314799

(51) Int. Cl.
*C09K 19/00* (2006.01)
*C09K 19/06* (2006.01)
*C09K 19/52* (2006.01)

(52) U.S. Cl. ........... 252/299.6; 252/299.01; 252/299.61; 252/299.62; 252/299.63; 252/299.64; 428/1.1; 349/1; 349/56; 349/182; 430/20

(58) Field of Classification Search ............. 252/299.01, 252/299.6, 299.61–299.64; 428/1.1; 349/1, 349/56, 182; 430/20
See application file for complete search history.

(56) References Cited

U.S. PATENT DOCUMENTS

| | | |
|---|---|---|
| 7,416,765 B2 * | 8/2008 | Seki et al. .................. 428/1.1 |
| 2008/0143926 A1 * | 6/2008 | Amimori et al. .............. 430/20 |

FOREIGN PATENT DOCUMENTS

| | | |
|---|---|---|
| JP | 3-9321 A | 1/1991 |
| JP | 2004-123597 A | 4/2004 |
| JP | 2004-123882 A | 4/2004 |
| JP | 2006-104307 A1 | 4/2006 |
| JP | 2007-070285 A | 3/2007 |
| JP | 2007-231108 A | 9/2007 |
| JP | 2007-286278 A | 11/2007 |

* cited by examiner

*Primary Examiner* — Geraldina Visconti
(74) *Attorney, Agent, or Firm* — Sughrue Mion, PLLC

(57) ABSTRACT

A polymerizable liquid crystal compound is represented by the following formula (1):

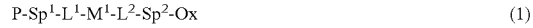

wherein P represents a polymerizable group; one of $Sp^1$ and $Sp^2$ represents a branched alkylene group, or an alkylene group containing, in the chain thereof, at least one divalent linking group selected from the group consisting of —O—, —C≡C— and —S—; the other of $Sp^1$ and $Sp^2$ represents a straight chain alkylene group; each of $L^1$ and $L^2$ independently represents a divalent linking group; $M^1$ represents a mesogenic group; and Ox represents a substituent containing an oxetanyl group.

12 Claims, 2 Drawing Sheets

POLYMERIZABLE LIQUID CRYSTAL COMPOUND, PHASE DIFFERENCE FILM AND LIQUID CRYSTAL DISPLAY USING THE SAME

TECHNICAL FIELD

The present invention relates to a polymerizable liquid crystal compound, and a phase difference film and a liquid crystal display using the same. More specifically, the invention relates to a polymerizable liquid crystal compound excellent in solubility in an organic solvent such as methyl ethyl ketone (MEK), and a phase difference film and a liquid crystal display using the same.

BACKGROUND ART

In recent years, optical films comprising a liquid crystal composition containing a liquid crystal compound have been used in optical compensation use and viewing angle widening use of a liquid crystal display. As the manufacturing method of an optical film comprising a liquid crystal composition, e.g., a method of forming a thin film of a liquid crystal composition on a substrate having an oriented film, followed by orientating the liquid crystal by heating to manufacture a film is reported (refer to JP-A-3-9321 (The term "JP-A" as used herein refers to an "unexamined published Japanese patent application".)). The monomers for use in forming an optical film are disclosed, for example, in JP-A-2004-123597 and JP-A-2004-123882.

DISCLOSURE OF THE INVENTION

Since both spacer parts (parts corresponding to $Sp^1$ and $Sp^2$) of the liquid crystal monomers disclosed in JP-A-2004-123597 and JP-A-2004-123882 comprise straight chain alkylene, solubility is low when the liquid crystal monomers are tried to be dissolved in an organic solvent suitable for continuous coating such as MEK (methyl ethyl ketone), so that the concentration of a solution cannot be heightened. Continuous coating with a coating solution low in viscosity results in deterioration of coated surface properties such as generation of unevenness and streaks. Further, there are such drawbacks that when solubility is increased by the introduction of a methyl group into the benzene ring of a mesogen part (a part corresponding to $M^1$), orientation cannot be sufficiently stabilized even after the polymerization and orientation of the liquid crystal is disturbed by heating, as a result a necessary optical characteristic (retardation) as a phase difference film cannot be retained.

Accordingly, an object of the invention is to provide a polymerizable liquid crystal compound having excellent solubility in an organic solvent (MEK, and the like), and further objects are to provide a phase difference film and a liquid crystal display using the same.

As a result of earnest examination of the present inventors for solving the above problems, it has been found that the above problems can be solved by introducing certain specific structures to the two spacer groups constituting a polymerizable liquid crystal compound (a monomer), thus the invention has been achieved.

The means for solving the above problems are as follows.

<1> A polymerizable liquid crystal compound represented by the following formula (1):

$$P\text{-}Sp^1\text{-}L^1\text{-}M^1\text{-}L^2\text{-}Sp^2\text{-}Ox \quad (1)$$

wherein

P represents a polymerizable group;

one of $Sp^1$ and $Sp^2$ represents a branched alkylene group, or an alkylene group containing, in the chain thereof, at least one divalent linking group selected from the group consisting of —O—, —C≡C— and —S—;

the other of $Sp^1$ and $Sp^2$ represents a straight chain alkylene group;

each of $L^1$ and $L^2$ independently represents a divalent linking group;

$M^1$ represents a mesogenic group having at least one divalent group selected from the group consisting of the following formulae (2-1) to (2-12); and Ox represents a group represented by the following formula (3):

(2-1)

(2-2)

(2-3)

(2-4)

(2-5)

(2-6)

(2-7)

(2-8)

(2-9)

(2-10)

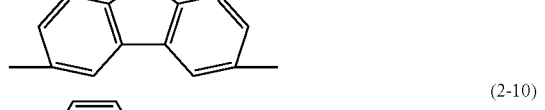

(2-11)

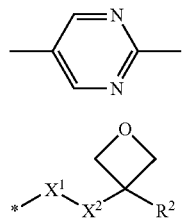

(2-12)

(3)

wherein
R² represents a hydrogen atom, a methyl group or an ethyl group;
X¹ represents —O—, —S—, —OCO— or —COO—;
X² represents a single bond or an alkylene group having from 1 to 4 carbon atoms; and
* is a bonding site to Sp².

<2> The polymerizable liquid crystal compound as described in <1>, wherein
one of Sp¹ and Sp² represents an alkylene group containing —O— or —C≡C— in the chain thereof <3> The polymerizable liquid crystal compound as described in <2>, wherein
the alkylene group containing —O— or —C≡C— in the chain thereof is represented by —(CH₂)$_{n1}$—X—(CH₂)$_{n2}$—
wherein
each of n1 and n2 independently represents an integer of from 1 to 4; and
—X— represents —O— or —C≡C—.

<4> The polymerizable liquid crystal compound as described in any of <1> to <3>, wherein
Sp² is a straight chain alkylene group.

<5> The polymerizable liquid crystal compound as described in any of <1> to <4>, wherein
P represents a (meth)acryloyloxy group or a (meth)acryloyl group.

<6> The polymerizable liquid crystal compound as described in any of <1> to <5>, wherein
each of L¹ and L² independently represents a single bond, —O—, —S—, —OCO—, —COO—, —CO—, —CH₂—, —CONH— or —NHCO—.

<7> The polymerizable liquid crystal compound as described in <6>, wherein
each of L¹ and L² independently represents —O—.

<8> The polymerizable liquid crystal compound as described in any of <1> to <7>, wherein
M¹ is a group represented by the following formula (5):

-Hex¹-Sp³-Hex²-Sp⁴-Hex³-    (5)

wherein
each of Hex¹, Hex², and Hex³ independently represents a substituted or unsubstituted 1,4-phenylene group, or a substituted or unsubstituted 1,4-cyclohexylene group; and
each of Sp³ and Sp⁴ independently represents a single bond, —OCO—, —COO—, or an acetylene group.

<9> The polymerizable liquid crystal compound as described in <8>, wherein
one of Sp³ and Sp⁴ represents —COO—; and
the other of Sp³ and Sp⁴ represents —OCO—.

<10> The polymerizable liquid crystal compound as described in <8> or <9>, wherein
each of Hex¹, Hex², and Hex³ independently represents a substituted or unsubstituted 1,4-phenylene group.

<11> The polymerizable liquid crystal compound as described in any of <1> to <10>, wherein
X¹ represents —O—; and
X² represents methylene.

<12> A composition containing the polymerizable liquid crystal compound as described in any of <1> to <11>.

<13> A phase difference film, which is formed with the composition as described in <12>.

<14> The phase difference film as described in <13>, which has pattern-like phase difference.

<15> A liquid crystal display, comprising the phase difference film as described in <13> or <14>.

BEST MODE FOR CARRYING OUT THE INVENTION

Figure 1A:
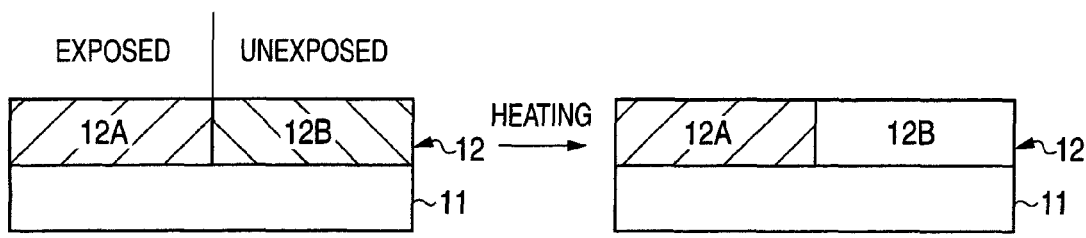
FIGS. 1A, 1B, 1C, 1D and 1E are the outline of the cross sectional view of examples of the substrates for the liquid crystal display in the invention.

In the specification of the invention, "from (numerical value x) to (numerical value y)" means to include both numerical values as the greatest lower bound and the least upper bound, respectively.

The polymerizable liquid crystal compound of the invention is described in detail below. The polymerizable liquid crystal compound is represented by the following formula (1):

P-Sp¹-L¹-M¹-L²-Sp²-Ox    (1)

In formula (1), P represents a polymerizable group. In the specification of the invention, when —CO—, —OCO— and —COO— are bonded to the polymerizable double bond in the polymerizable group P, the group is also defined as polymerizable group P including —CO—, —OCO— and —COO—. The polymerizable group in the invention is not especially restricted so long as the group is a polymerizable functional group, but it is preferably a radical polymerizable group. The later-described Ox is a cationic polymerizable group, so that by making it as a radical polymerizable group, polymerization reaction can be advanced under different condition. For example, the later-described patterning of phase difference can be easily performed. The examples of radical polymerizable groups preferably include a (meth)acryloyloxy group or a (meth)acryloyl group, and more preferably a(meth)acryloyloxy group.

In formula (1), either Sp¹ or Sp² represents branched alkylene, or alkylene containing at least one divalent linking group selected from the group consisting of —O—, —C≡C— and —S— in the chain, and the other represents straight chain alkylene. By making $Sp^1$ and $Sp^2$ different structures like this, i.e., an asymmetric structure, the solubility of the compound in an organic solvent, in particular in MEK, etc., is improved. Of the branched alkylene, and the alkylene containing at least one divalent linking group selected from the group consisting of —O—, —C≡C— and —S— in the chain, alkylene containing —O— or —C≡C— in the chain is preferred, and alkylene represented by —(CH$_2$)$_{n1}$—X—(CH$_2$)$_{n2}$— is more preferred, where n1 and n2 each represents an integer of from 1 to 4, and preferably 1 or 2. —X— represents —O— or —C≡C—, and preferably —O—. When —X— represents —O—, n1 and n2 both preferably represent 2, and when —X— represents —C≡C—, n1 and n2 both preferably represent 1. The number of carbon atoms of the branched alkylene (including the carbon atoms of the branched chains) is preferably from 4 to 12, more preferably from 4 to 8, and still more preferably from 4 to 6. As the branched chain, a methyl group and an ethyl group are preferred, and a methyl group is more preferred.

The number of carbon atoms of the other straight chain alkylene is preferably from 2 to 12, more preferably from 4 to 8, and still more preferably from 4 to 6. The selection as to which of the two of branched alkylene or alkylene containing at least one divalent linking group selected from the group consisting of —O—, —C≡C— and —S— in the chain, and straight chain alkylene is to be carried by $Sp^1$ or $Sp^2$ is not especially restricted, which can be arbitrarily selected depending upon the usage and the using method. For example, it is preferred to select them according to the order in the polymerization reaction of a polymerizable groups P and -Ox. For example, when -Ox is polymerized first, it is preferred that $Sp^2$ is straight chain alkylene and $Sp^1$ is branched alkylene, or alkylene containing at least one divalent linking group selected from the group consisting of —O—, —C≡C— and —S— in the chain. Contrary to this, when a polymerizable group P is polymerized first, it is preferred that $Sp^1$ is straight chain alkylene and $Sp^2$ is branched alkylene, or alkylene containing at least one divalent linking group selected from the group consisting of —O—, —C≡C— and —S— in the chain. When polymerization is carried out stepwise like this, the second polymerization is low in fluidity as compared with the first polymerization, so that the rate of polymerization tends to lower. From this fact, when the spacer on the side of the polymerizable group polymerized first is branched alkylene, or alkylene containing at least one divalent linking group selected from the group consisting of —O—, —C≡C— and —S— in the chain, the mesogen part is liable to thermally fluctuate, as a result heat resistance is decreased. Accordingly, when the spacer on the side of the polymerizable group polymerized first is straight chain alkylene, the thermal fluctuation of the mesogen part is restrained, and heat resistance is bettered. Heat resistance becomes important in forming a phase difference film having pattern-like phase difference in the method including a heating process described in detail later.

In formula (1), $L^1$ and $L^2$ each represents a divalent linking group. $L^1$ and $L^2$ are not especially restricted so long as they are groups linking $Sp^1$ and $M^1$, and $Sp^2$ and $M^1$, but $L^1$ and $L^2$ each preferably represents a single bond, —O—, —S—, —OCO—, —COO—, —CO—, —CH$_2$—, —CONH— or —NHCO—, more preferably a single bond, —O—, —S—, —OCO— or —COO—, still more preferably a single bond, —O— or —CH$_2$—, and most preferably —O—. It is preferred that $L^1$ and $L^2$ represent the same divalent linking group, and it is more preferred for both of $L^1$ and $L^2$ to represent —O—. Incidentally, in the specification of the invention, in the case where —O— is directly bonded to $M^1$, the —O— is taken as $L^1$ or $L^2$, not to constitute $Sp^1$ or $Sp^2$.

In formula (1), $M^1$ represents a mesogenic group having at least one divalent group selected from the group consisting of the following formulae (2-1) to (2-12), preferably having 3 or more divalent groups, and more preferably having 3 divalent groups. By bringing the number of the divalent group selected from the group consisting of the following formulae (2-1) to (2-12) into the above range, it becomes easy to get a liquid crystal property and form a film having pattern-like phase difference.

(2-1)

(2-2)

(2-3)

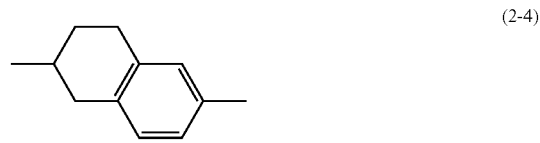

(2-4)

(2-5)

(2-6)

(2-7)

(2-8)

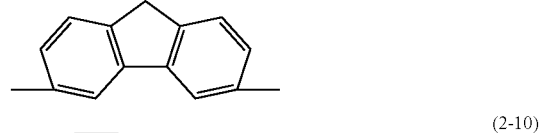

(2-9)

(2-10)

(2-11)

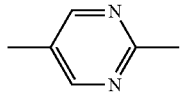
(2-12)

The divalent group represented by formula (2-1) is an unsubstituted 1,4-cyclohexylene group, and the divalent group represented by formula (2-2) is an unsubstituted 1,4-phenylene group.

When the mesogenic group represented by $M^1$ consists of 2 or more of the above groups, these groups are sufficient to be bonded by a linking group selected from the group consisting of a single bond, an acetylene group (—C≡C—), —N=N—, —N=CH—, —C(CN)=CH—, —CONH-CONHCO—, —O—, —S—, —OCO—, —COO—, —OCOO—, —CO—, —CH2—, —OCH$_2$—, —CH$_2$O—, —CONH—, —NHCO—, —NHCOO—, and —OCONH—, preferably they are sufficient to be bonded by a linking group selected from the group consisting of a single bond, an acetylene group (—C≡C—), —OCO—, —COO—, —OCH$_2$—, —CH$_2$O—,—N=N—, —N=CH—, —C(CN)=CH—, —CONH—, —NHCO—, and —CONHCONHCO—, and more preferably they suffice to be bonded by a linking group selected from the group consisting of a single bond, an acetylene group (—C≡C—), —OCO—, —COO—, —CONH—, and —NHCO—.

Each of the divalent groups represented by any of the above formulae (2-1) to (2-12) may have a substituent. It is preferred that the substituents be such that the polymerizable liquid crystal compound represented by formula (1) shows a liquid crystal property. The examples of the substituents include an alkyl group (preferably an alkyl group having from 1 to 20 carbon atoms, more preferably from 1 to 12, and especially preferably from 1 to 8, e.g., a methyl group, an ethyl group, an isopropyl group, a tert-butyl group, an n-octyl group, an n-decyl group, an n-hexadecyl group, a cyclopropyl group, a cyclopentyl group, a cyclohexyl group, etc., are exemplified), an alkenyl group (preferably an alkenyl group having from 2 to 20 carbon atoms, more preferably from 2 to 12, and especially preferably from 2 to 8, e.g., a vinyl group, an allyl group, a 2-butenyl group, a 3-pentenyl group, etc., are exemplified), an alkynyl group (preferably an alkynyl group having from 2 to 20 carbon atoms, more preferably from 2 to 12, and especially preferably from 2 to 8, e.g., a propargyl group, a 3-pentynyl group, etc., are exemplified), an aryl group (preferably an aryl group having from 6 to 30 carbon atoms, more preferably from 6 to 20, and especially preferably from 6 to 12, e.g., a phenyl group, a p-methylphenyl group, a naphthyl group, etc., are exemplified), a substituted or unsubstituted amino group (preferably an amino group having from 0 to 20 carbon atoms, more preferably from 0 to 10, and especially preferably from 0 to 6, e.g., an unsubstituted amino group, a methylamino group, a dimethylamino group, a diethylamino group, a benzylamino group, etc., are exemplified), an alkoxyl group (preferably an alkoxyl group having from 1 to 20 carbon atoms, more preferably from 1 to 12, and especially preferably from 1 to 8, e.g., a methoxy group, an ethoxy group, a butoxy group, etc., are exemplified), an aryloxy group (preferably an aryloxy group having from 6 to 20 carbon atoms, more preferably from 6 to 16, and especially preferably from 6 to 12, e.g., a phenyloxy group, a 2-naphthyloxy group, etc., are exemplified), an acyl group (preferably an acyl group having from 1 to 20 carbon atoms, more preferably from 1 to 16, and especially preferably from 1 to 12, e.g., an acetyl group, a benzoyl group, a formyl group, a pivaloyl group, etc., are exemplified), an alkoxycarbonyl group (preferably an alkoxycarbonyl group having from 2 to 20 carbon atoms, more preferably from 2 to 16, and especially preferably from 2 to 12, e.g., a methoxycarbonyl group, an ethoxycarbonyl group, etc., are exemplified), an aryloxycarbonyl group (preferably an aryloxycarbonyl group having from 7 to 20 carbon atoms, more preferably from 7 to 16, and especially preferably from 7 to 10, e.g., a phenyloxycarbonyl group, etc., are exemplified), an acyloxy group (preferably an acyloxy group having from 2 to 20 carbon atoms, more preferably from 2 to 16, and especially preferably from 2 to 10, e.g., an acetoxy group, a benzoyloxy group, etc., are exemplified), an acylamino group (preferably an acylamino group having from 2 to 20 carbon atoms, more preferably from 2 to 16, and especially preferably from 2 to 10, e.g., an acetylamino group, a benzoylamino group, etc., are exemplified), an alkoxycarbonylamino group (preferably an alkoxycarbonylamino group having from 2 to 20 carbon atoms, more preferably from 2 to 16, and especially preferably from 2 to 12, e.g., a methoxycarbonylamino group, etc., are exemplified), an aryloxycarbonylamino group (preferably an aryloxycarbonylamino group having from 7 to 20 carbon atoms, more preferably from 7 to 16, and especially preferably from 7 to 12, e.g., a phenyloxycarbonylamino group, etc, are exemplified), a sulfonylamino group (preferably a sulfonyl-amino group having from 1 to 20 carbon atoms, more preferably from 1 to 16, and especially preferably from 1 to 12, e.g., a methanesulfonylamino group, a benzenesulfonylamino group, etc, are exemplified), a sulfamoyl group (preferably a sulfamoyl group having from 0 to 20 carbon atoms, more preferably from 0 to 16, and especially preferably from 0 to 12, e.g., a sulfamoyl group, a methylsulfamoyl group, a dimethylsulfamoyl group, a phenylsulfamoyl group, etc, are exemplified), a carbamoyl group (preferably a carbamoyl group having from 1 to 20 carbon atoms, more preferably from 1 to 16, and especially preferably from 1 to 12, e.g., an unsubstituted carbamoyl group, a methylcarbamoyl group, a diethylcarbamoyl group, a phenylcarbamoyl group, etc., are exemplified), an alkylthio group (preferably an alkylthio group having from 1 to 20 carbon atoms, more preferably from 1 to 16, and especially preferably from 1 to 12, e.g., a methylthio group, an ethylthio group, etc., are exemplified), an arylthio group (preferably an arylthio group having from 6 to 20 carbon atoms, more preferably from 6 to 16, and especially preferably from 6 to 12, e.g., a phenylthio group, etc., are exemplified), a sulfonyl group (preferably a sulfonyl group having from 1 to 20 carbon atoms, more preferably from 1 to 16, and especially preferably from 1 to 12, e.g., a mesyl group, a tosyl group, etc., are exemplified), a sulfinyl group (preferably a sulfinyl group having from 1 to 20 carbon atoms, more preferably from 1 to 16, and especially preferably from 1 to 12, e.g., a methanesulfinyl group, a benzenesulfinyl group, etc., are exemplified), a ureido group (preferably a ureido group having from 1 to 20 carbon atoms, more preferably from 1 to 16, and especially preferably from 1 to 12, e.g., an unsubstituted ureido group, a methylureido group, a phenyl-ureido group, etc., are exemplified), a phosphoric amido group (preferably a phosphoric amido group having from 1 to 20 carbon atoms, more preferably from 1 to 16, and especially preferably from 1 to 12, e.g., a diethylphosphoric amido group, a phenylphosphoric amido group, etc., are exemplified), a hydroxyl group, a mercapto group, a halogen atom (e.g., a fluorine atom, a chlorine atom, a bromine atom, an iodine atom), a cyano group, a sulfo group, a carboxyl group, a nitro group, a hydroxamic acid group, a sulfino group, a hydrazino group, an imino group, a heterocyclic group (preferably a heterocyclic group having from 1 to 30 carbon atoms, and more preferably from 1 to 12, e.g., a heterocyclic group having a hetero atom, such as a nitrogen atom, an oxygen atom, a sulfur atom, etc., e.g., an imidazolyl group, a pyridyl group, a quinolyl group, a furyl group, a piperidyl group, a morpholino group, a benzoxazolyl group, a benzimidazolyl group, a benzothiazolyl group, etc., are exemplified), and a silyl group(preferably a silyl group having from 3 to 40 carbon atoms, more preferably from 3 to 30, and especially preferably from 3 to 24, e.g., a trimethylsilyl group, a triphenylsilyl group, etc., are exemplified). These substituents may further be substituted with these substituents.

Of the above substituents, a halogen atom, a carboxyl group, an alkyl group having from 1 to 8 carbon atoms, a halogen-substituted alkyl group having from 1 to 8 carbon atoms, and an alkyl group having from 1 to 8 carbon atoms substituted with a carboxyl group are preferably exemplified, a fluorine atom, a chlorine atom, a carboxyl group, a methyl group, and a fluorine-substituted methyl group are more preferably exemplified, and a fluorine atom is still more preferred. Groups not having a substituent are preferred to groups having a substituent. When $M^1$ comprises a plurality of formulae (2-1) to (2-12), it is preferred that all the groups do not have a substituent.

When the mesogen part is an unsubstituted group, packing of the mesogen part with each other becomes strong, so that the heat resistance tends to be higher as compared with the case of the same rate of polymerization. Therefore, in view of heat resistance, it is preferred that the mesogen part is free from an unsubstituted group. From the same reason, in the light of heat resistance, a group hard to move such as a phenyl group is preferred to a group easy to move such as a 1,4-cyclohexylene group. By taking such a structure, it is easy to form a film having pattern-like phase difference as described later.

$M^1$ is preferably a group represented by the following formula (5):

$$-\text{Hex}^1-\text{Sp}^3-\text{Hex}^2-\text{Sp}^4-\text{Hex}^3- \qquad (5)$$

In formula (5), $\text{Hex}^1$, $\text{Hex}^2$, and $\text{Hex}^3$ each represents a substituted or unsubstituted 1,4-phenylene group (2-2), or a substituted or unsubstituted 1,4-cyclohexylene group (2-1), and $\text{Sp}^3$ and $\text{Sp}^4$ each represents a single bond, —OCO—, —COO—, or an acetylene group. Further, it is preferred for $\text{Sp}^3$ to represent —COO— and $\text{Sp}^4$ represent —OCO—, or for $\text{Sp}^3$ to represent —OCO— and $\text{Sp}^4$ represent —COO—, and it is more preferred for $\text{Sp}^3$ to represent —COO— and $\text{Sp}^4$ represent —OCO—. Moreover, $\text{Hex}^1$, $\text{Hex}^2$, and $\text{Hex}^3$ each preferably represents a substituted or unsubstituted 1,4-phenylene group, and more preferably an unsubstituted 1,4-phenylene group.

As the mesogenic groups represented by Ml, the following groups are preferably exemplified.

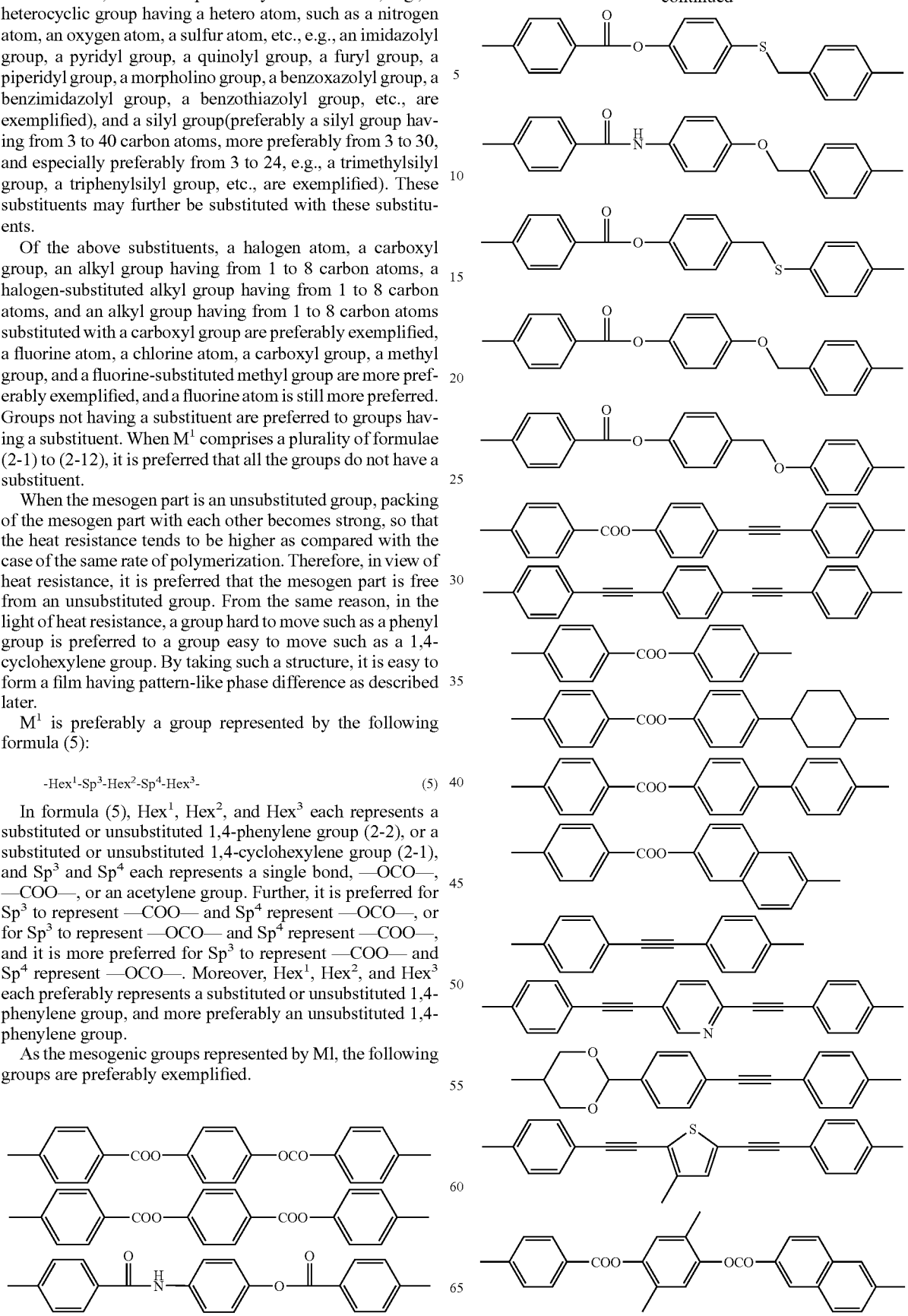

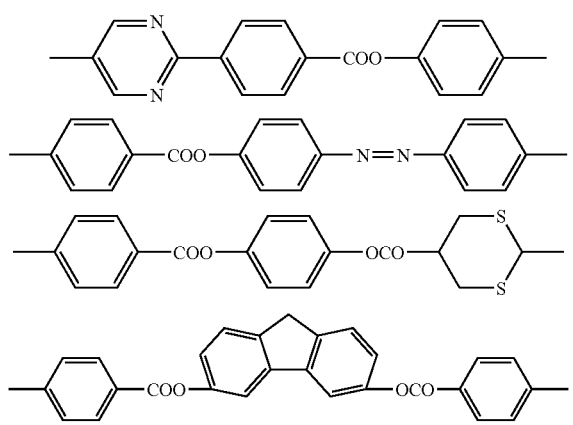

Of these groups, the following structures are more preferred.

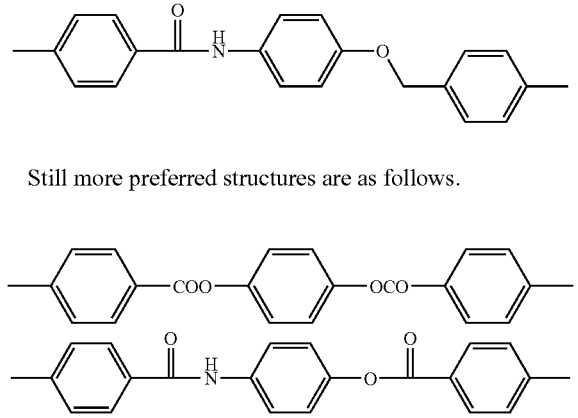

Still more preferred structures are as follows.

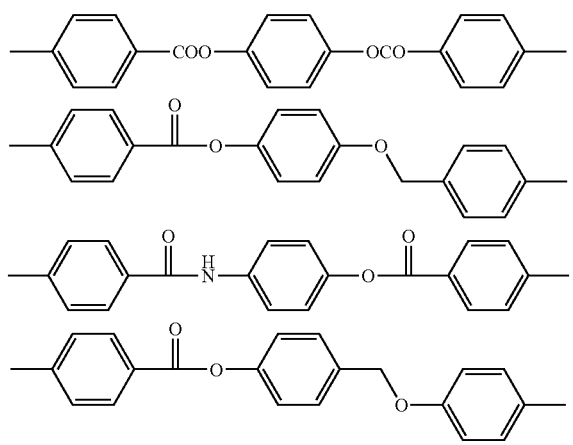

In formula (1), Ox represents a group represented by the following formula (3).

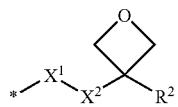

(3)

In formula (3), $R^2$ represents a hydrogen atom, a methyl group or an ethyl group, preferably a methyl group or an ethyl group, and more preferably a methyl group. $X^1$ represents —O—, —S—, —OCO— or —COO—, preferably —O— or —OCO— (O is on the Ox side and CO is on the Sp side), and more preferably —O—. $X^2$ represents a single bond or alkylene having from 1 to 4 carbon atoms, preferably alkylene having from 1 or 2 carbon atoms, and more preferably alkylene (methylene) having 1 carbon atom. * is a bonding site to $Sp^2$.

As a polymerizable group represented by formula (1) having an oxetanyl group, the following compounds can be preferably exemplified.

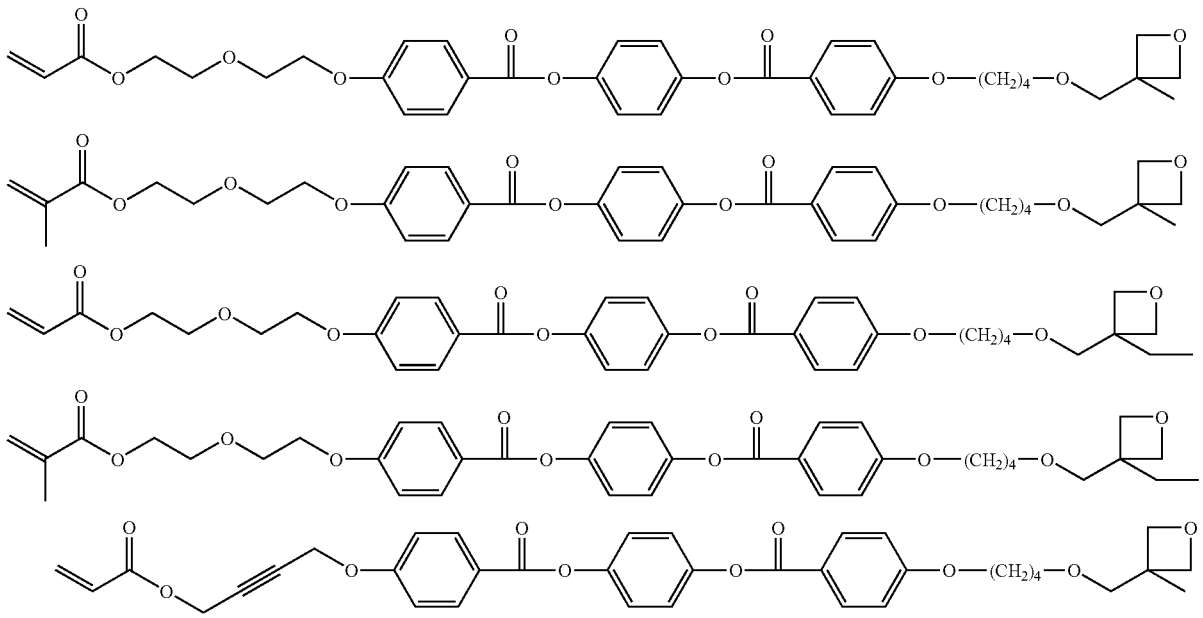

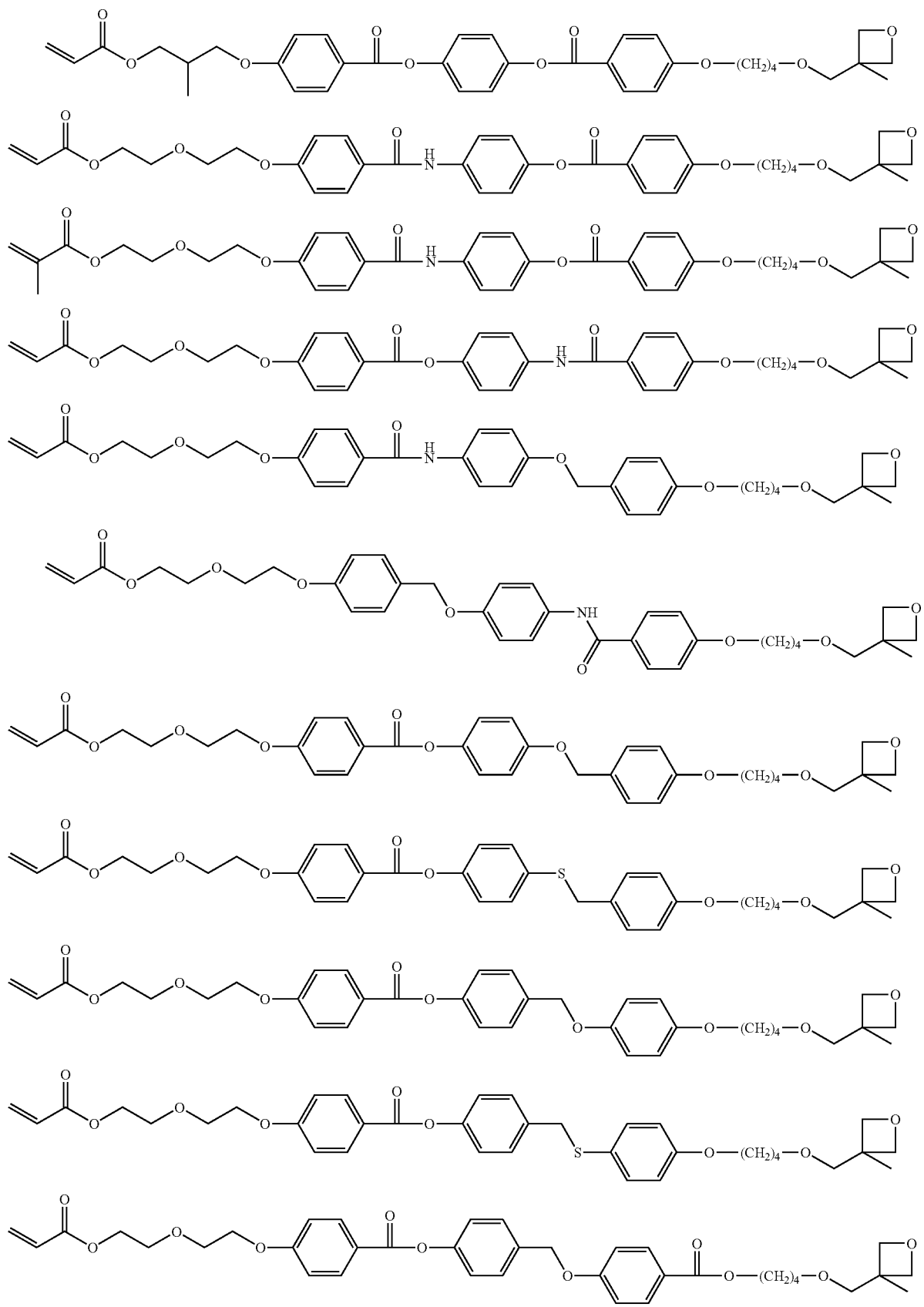

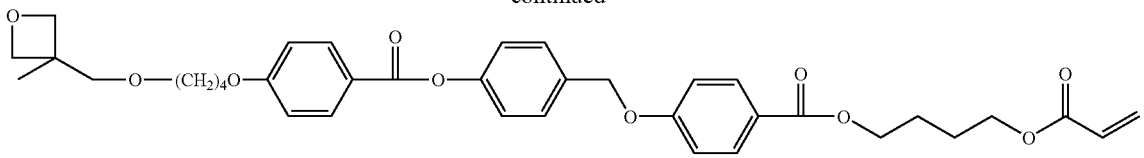

A polymerizable liquid crystal group having an oxetanyl group can be synthesized by the application of any method used in ordinary organic chemical synthesizing methods with no particular limitation. For example, a (meth)acryloyl compound having an oxetanyl group having two reactive functional groups of an oxetanyl group and a (meth)acryl group can be synthesized by linking a part having an oxetanyl group and a part having a (meth)acryl group by means of Williamson's synthesis of ether or synthesis of ester using a condensing agent. In the synthesis, the methods disclosed in JP-A-2004-123597 and JP-A-2004-123882 can be referred to.

An example of synthesizing methods is shown below.

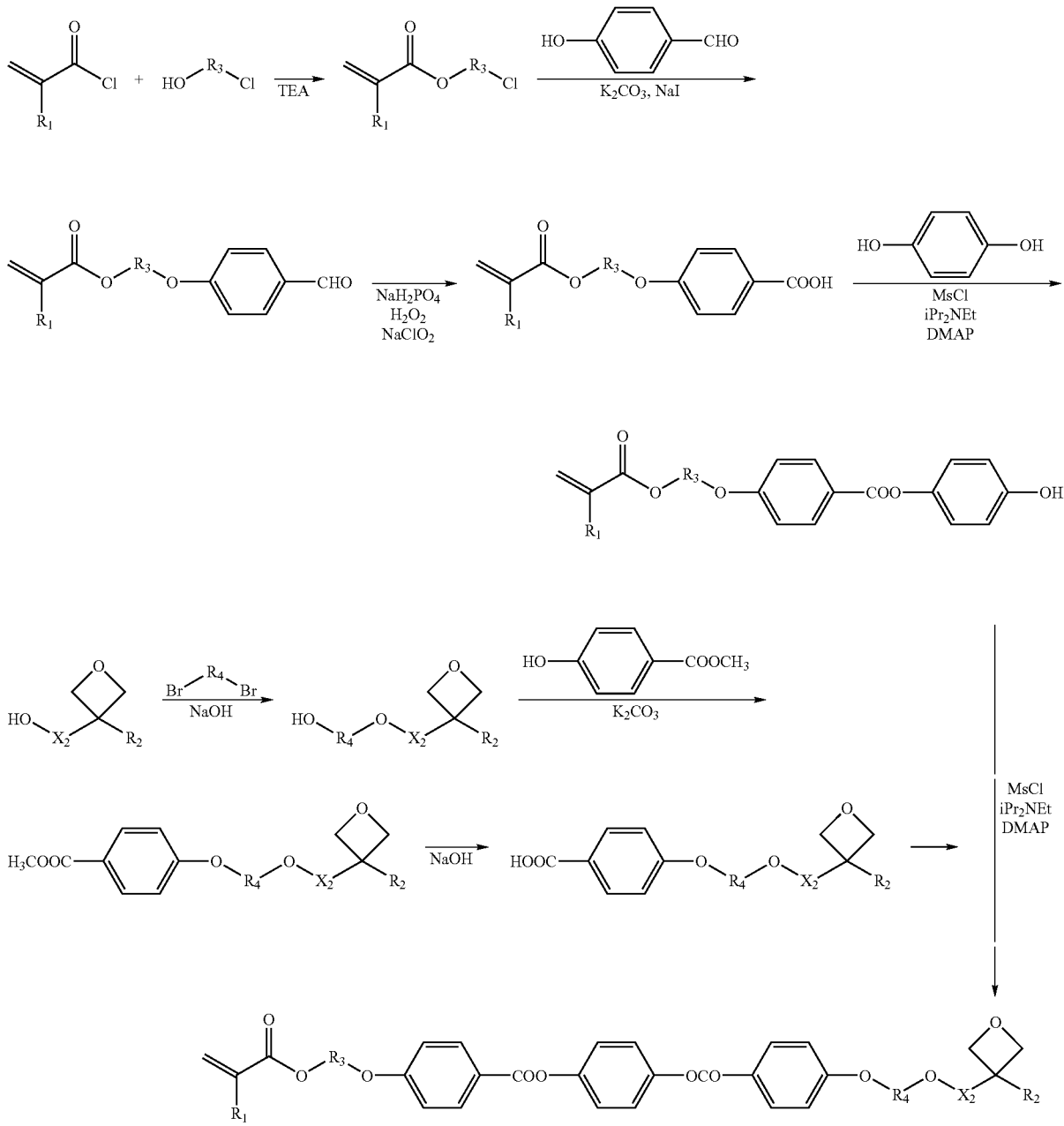

The abbreviations in the above formulae are as follows.
MsCl: Methanesulfonyl chloride
iPr$_2$NEt: Diisopropylethylamine
DMAP: 4,-Dimethylaminopyridine
TEA: Triethylamine The composition in the invention is bound to have the above polymerizable liquid crystal compound. A phase difference film can be manufactured with the composition, and a phase difference film having pattern-like phase difference can be preferably formed. A phase difference film having pattern-like phase difference can be preferably used in a semi-transmission type liquid crystal display (a semi-transmission type LCD).

One terminal of the polymerizable liquid crystal compound is an oxetanyl group, and when the other terminal is made a radical polymerizable group, e.g., a (meth)acryloyl group, the monomer becomes a bifunctional monomer having the cationic polymerizable oxetanyl group and the radical polymerizable (meth)acryloyl group. Accordingly, in a liquid crystal composition containing such a monomer, it becomes possible to polymerize the (meth)acryloyl group alone by radical polymerization and to polymerize the oxetanyl group alone by cationic polymerization. That is, a liquid crystal film little in turbulence of orientation after stabilization of orientation and high in thermal stability can be manufactured.

Further, after coating a liquid crystal composition obtained by adding a photo-acid generator to such a monomer on a substrate with an oriented film and subjecting to light irradiation in the atmospheric air, cationic polymerization advances and the oxetanyl group is polymerized and, in addition, radical polymerization of a part of (meth)acryloyl group also progresses, so that orientation can be stabilized. However, since the rate of polymerization is low in the atmospheric air, heat resistance is low, orientation is disturbed by heating, as a result the reaction product becomes isotropic. Patterning of a phase difference film is possible with the utilization of this fact.

It is also possible to form an orientation stabilized liquid crystal film having been subjected to patterning by advancing different polymerizations separately. The methods as shown below are exemplified as the specific examples of patterning, but the invention is by no means restricted to these methods.

1) A liquid crystal composition comprising a polymerizable liquid crystal compound, a photo-radical generator, and a photo-acid generator is coated on an oriented film. After raising the temperature to a temperature range capable of showing a liquid crystal property, the coating is irradiated with light of the wavelength to which only the photo-radical generator has absorption to advance radical polymerization alone to obtain an optically anisotropic polymer. In the next place, pattern exposure is performed with light of the wavelength to which the photo-acid generator has absorption through a mask to advance cationic polymerization. A negative pattern can be obtained by immersing the film in a developing solution capable of dissolving the polymer obtained by advancing radical polymerization alone.

2) A liquid crystal composition comprising a polymerizable liquid crystal compound and a photo-radical generator is coated on an oriented film. After raising the temperature to a temperature range capable of showing a liquid crystal property, the coating is irradiated with light to advance radical polymerization alone to obtain an optically anisotropic polymer. In the next place, an organic solvent solution containing a photo-acid generator is coated thereon to impregnate the optically anisotropic polymer with the photo-acid generator. Exposure is performed through a mask to advance cationic polymerization. A negative pattern can be obtained by immersing the film in a developing solution capable of dissolving the polymer obtained by advancing radical polymerization alone.

3) A liquid crystal composition comprising a polymerizable liquid crystal compound and a photo-cation generator is coated on an oriented film. After raising the temperature to a temperature range capable of showing a liquid crystal property, the coating is irradiated with light to primarily advance cationic polymerization (radical polymerization partly progresses in many cases) to obtain an optically anisotropic polymer (partly crosslinked). In the next place, an organic solvent solution containing a photo-radical generator is coated thereon to impregnate the optically anisotropic polymer with the photo-radical generator. Exposure is performed through a mask to advance radical polymerization. A negative pattern can be obtained by heating the obtained optically anisotropic polymer film at 200° C. or so.

According to the pattering method in item 3), a functional substrate (a substrate having been patterned with retardation) can be formed without carrying out an immersion process by a developing solution. The method in item 3) will be described in detail.

In the following description, Re means in-plane retardation. Re ($\lambda$) is measured by the incidence of light of wavelength of X nm in the direction of normal line of a film with KOBRA 21ADH or WR (manufactured by Oji Scientific Instruments). Re in the invention means the ones measured at wavelengths of 611±5 nm, 545±5 nm and 435±5 nm with respect to R, G and B respectively, and means the ones measured at wavelength of 545±5 nm or 590±5 nm unless otherwise indicated concerning colors.

In the following description, in connection with angles, "substantially" means that the error from a strict angle is within the range of less than ±5°. The more preferred error from a strict angle is less than ±40, and less than ±30 is still more preferred. With respect to retardation, "substantially" means that the error of retardation is within ±5°. Further, "Re is not substantially 0" mean that "Re is not lower than 5 nm". Moreover, the measuring wavelength of a refractive index indicates arbitrary wavelength in visible rays, unless otherwise indicated. Incidentally, "visible rays" in the following description are rays of the wavelengths of from 400 to 700 nm.

Functional Substrate:

Functional substrate is a functional substrate having pattern-like retardation, which has a substrate, and an optically anisotropic layer having at least one layer of pattern-like retardation. "An optically anisotropic layer having pattern-like retardation" is "an optically anisotropic layer having areas different in retardation pattern-wise", and generally means "an optically anisotropic layer having an area of in-plane retardation of Re1 and an area of in-plane retardation of Re2 (Re1>Re2) pattern-wise". Further, in the following description, "a functional substrate" is used in distinction from "a substrate" unless otherwise indicated.

FIGS. 1A, 1B, 1C, 1D and 1E are the outline of the cross sectional view of several functional substrates. The functional substrate shown in FIG. 1A comprises substrate 11 having formed thereon optically anisotropic layer 12 having pattern-like retardation. Substrate 11 is not especially restricted so long as it is transparent, but a support low in double refraction is preferred, and glass, a low double refraction polymer and the like are generally used. Optically anisotropic layer 12 having pattern-like retardation is formed by the method described in the above step 3). According to this method, different display modes in a liquid crystal cell, in particular different optical compensations in a transmission part and reflection part of semi-transmission LCD, can be achieved. Further, different from conventional cases where an optically anisotropic layer is provided on a plastic support susceptible to dimensional fluctuation by temperature and humidity, when an optically anisotropic layer is provided in a cell, since the optically anisotropic layer is tenaciously sustained by a glass substrate, dimensional fluctuation by temperature and humidity is difficult to occur, and unevenness in corner of LCD can be improved.

Figure 1B:
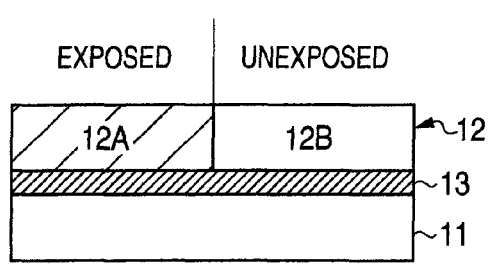
Figure 1C:
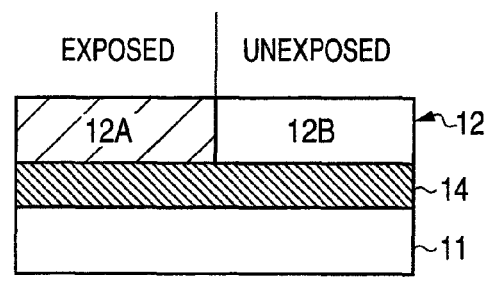
Figure 1D:
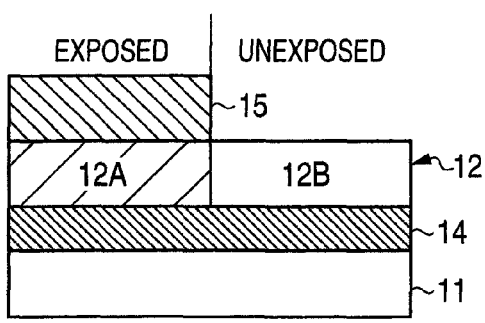
Figure 1E:
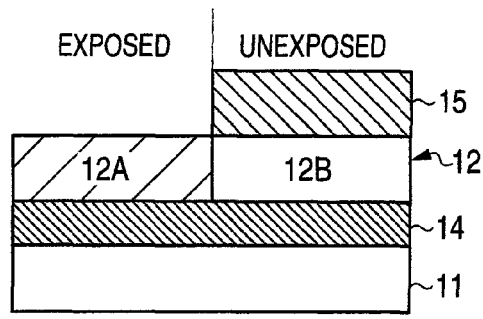
Figure 2A:
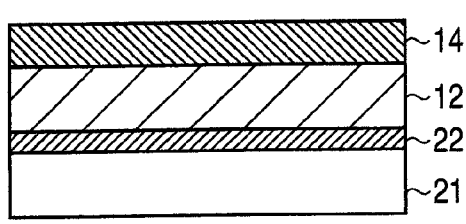
FIGS. 2A, 2B, 2C and 2D are the outline of the cross sectional view of examples of the transfer materials for use in the manufacturing method of the substrate for the liquid crystal display in the invention,
wherein
11 denotes Substrate, 12 denotes Optically anisotropic layer, 12A denotes Exposed part of optically anisotropic layer, 12B denotes Unexposed part of optically anisotropic layer, 13 denotes Orientation layer (on a substrate), 14 denotes Adhesive layer for transfer, 15 denotes Photosensitive resin layer, 21 denotes Dummy support, 22 denotes Orientation layer (on a dummy support), 23 denotes Mechanical characteristic controlling layer, and 24 denotes Dummy support for a transfer material to be transferred to dummy support 21.
Figure 2B:
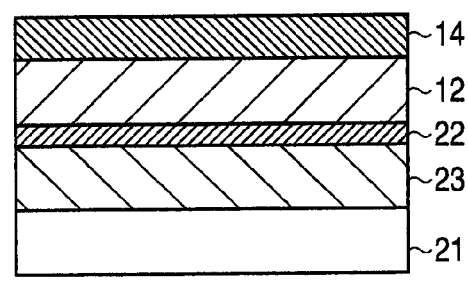
Figure 2C:
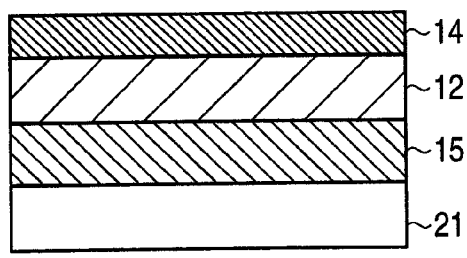

In the functional substrate shown in FIG. 1B, orientation layer 13 is formed between substrate 11 and optically anisotropic layer 12. After directly coating the material of optically anisotropic layer 12 on orientation layer 13 formed by rubbing a solution containing a liquid crystal compound, the coated layer is subjected to ripening and orientation at a liquid crystal-forming temperature, irradiated with heat or ionizing radiation while maintaining the above state as it is to be solidified and become optically anisotropic layer 12. Formation of areas different in retardation can be done in the same manner as above. In the functional substrate shown in FIG. 1C, adhesive layer 14 for transfer is formed between substrate 11 and optically anisotropic layer 12 having pattern-like retardation. This functional substrate can be manufactured with the materials for transfer as shown in FIG. 2A. The functional substrates shown in FIGS. 1D and 2E are embodiments comprising optically anisotropic layer 12 having provided thereon photosensitive resin layer 15. In FIG. 1D, a negative photosensitive resin and in (e) a positive photosensitive resin are respectively used. In either case, irregularity pattern can be formed at the same time with the exposure for the patterning of phase difference. These functional substrates can be manufactured by directly coating photosensitive resin layer 15, e.g., on the functional substrate shown in FIG. 1C, or with the transfer material as shown in FIG. 2C.

Figure 2D:
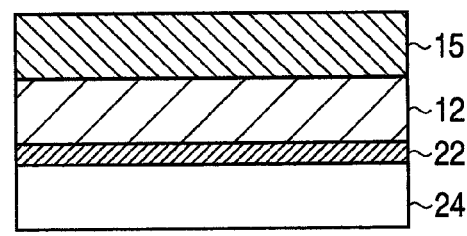

Transfer Material:

FIG. 2A is an example of a transfer material, and optically anisotropic layer 12 is formed on dummy support 21 with intervening orientation layer 22. Adhesive layer 14 for transfer is formed on optically anisotropic layer 12, and the functional substrate can be formed by lamination transferring of a transfer material on the substrate with intervening adhesive layer 14 for transfer. The adhesive layer for transfer is not especially restricted so long as the layer has a sufficient transferring property, and an adhesive layer by an adhesive, a photosensitive resin layer, a pressure-sensitive resin layer, a heat-sensitive resin layer are exemplified. Photosensitive or heat-sensitive resin layers are preferred in view of baking resistance that is required of a functional substrate. For giving a good transferring property, it is preferred that the peeling ability between optically anisotropic layer 12 and orientation layer 22 is high. FIG. 2B is an embodiment having mechanical characteristic controlling layer 23 for the prevention of mixture of babbles and absorption of unevenness on the functional substrate in a transfer process. As the mechanical characteristic controlling layer, those showing flexible elasticity, capable of softening by heat, and showing flowability by heat are preferred. FIG. 2C is a transfer material capable of manufacturing the functional substrate shown in FIG. 1D or 1E. FIG. 2C has photosensitive resin layer 15 for forming unevenness under optically anisotropic layer 12. For manufacturing the substrate in this embodiment, it becomes necessary to orientate a liquid crystal compound on photosensitive resin layer 15. When a coating solution containing a liquid crystal compound is coated on a photosensitive resin layer with an organic solvent, the photosensitive resin layer is generally dissolved due to the organic solvent, and the liquid crystal compound cannot be orientated. Accordingly, a transfer material as shown in FIG. 2D is formed on other dummy support 24, and photosensitive resin layer 15 also functions as a transfer adhesive layer to dummy support 24, thus adhesive layer 14 for transfer can be formed on optically anisotropic layer 12.

Substrate:

A substrate for use in the manufacture of a functional substrate is not especially restricted so long as it is transparent, and known glass plates, such as a soda glass plate having a silicate oxide film on the surface, heat resistance glass, non-alkali glass, a quartz glass plate, etc., and transparent substrates comprising polymers can be used. In the case of the use for a liquid crystal display, a high temperature process of 180° C. or more is required for the baking of a color filter and an oriented film in a manufacturing process of a functional substrate, so that substrates having heat resistance are preferably used. As such heat resistance substrates, a glass plate, or polyimide, polyether sulfone, heat resisting polycarbonate, polyethylene naphthalate are preferred, and glass plates are especially preferred from the viewpoint of price, transparency and heat resistance. Further, by subjecting a substrate to coupling treatment in advance, adhesion with a transfer adhesive layer can be bettered. As the coupling treatment, the method disclosed in JP-A-2000-39033 can be preferably used. Incidentally, although not limitative, the thickness of a substrate is generally preferably from 100 to 1,200 μm, and especially preferably from 300 to 1,000 μm.

A substrate for use in the manufacture of the functional substrate may be a color filter substrate having a color filter layer on the above glass substrate.

Dummy Support:

A dummy support for use in a transfer material is not especially restricted and may be transparent or opaque. The examples of the polymers constituting a dummy support include cellulose ester (e.g., cellulose acetate, cellulose propionate, cellulose butyrate), polyolefin (e.g., norbornene polymer), poly(meth)acrylic ester (e.g., polymethyl methacrylate), polycarbonate, polyester, polysulfone, and norbornene polymer. For the purpose of inspection of optical characteristics during the manufacturing process, transparent and low double refraction materials are preferred as a transparent support. From the viewpoint of low double refraction, cellulose ester and norbornene polymers are preferred. As commercially available norbornene polymers, ARTON (manufactured by JSR), ZEONEX® and ZEONOR® (manufactured by Zeon Corporation) can be used. Inexpensive polycarbonate and polyethylene terephthalate are also preferably used.

Optically Anisotropic Layer:

An optically anisotropic layer comprising a composition containing a liquid crystal compound is not especially restricted so long as it has at least one incident direction of Re that is substantially not 0 when phase difference is measured at an exposed part, i.e., it has optical characteristics of not isotropic.

It is preferred to form an optically anisotropic layer by coating a coating solution containing a polymerizable liquid crystal compound of the invention and other additives shown below on the later-described prescribed orientation layer. Organic solvents are preferably used as the solvent for use in the preparation of a coating solution. The examples of organic solvents include amide (e.g., N,N-dimethylformamide), sulfoxide (e.g., dimethyl sulfoxide), heterocyclic compounds (e.g., pyridine), hydrocarbon (e.g., benzene, hexane), alkyl halide (e.g., chloroform, dichloromethane), ester (e.g., methyl acetate, butyl acetate), ketone (e.g., methyl ethyl ketone), and ether (e.g., tetrahydrofuran, 1,2-dimethoxyethane). Alkyl halide and ketone are preferably used. Two or more solvents may be used in combination.

In a composition, the concentration of a polymerizable liquid crystal compound of the invention is preferably from 30 to 99.9 mass % to the total mass of the liquid crystal composition, more preferably from 50 to 99.9 mass %, and still more preferably from 70 to 99.9 mass %.

Any compounds can be used as a photo-acid generator so long as they can generate an acid upon irradiation with light and have an action of initiating the cationic polymerization of an oxetanyl group, but onium salts are preferably used. In this case, the counter anion may be either an organic anion or an inorganic anion. As the onium salts, an iodonium salt, a diazonium salt, a sulfonium salt are exemplified. Of these onium salts, a sulfonium salt and an iodonium salt are preferred, and an iodonium salt is more preferred in view of heat stability. As the representative photo-acid generators, the following compounds are exemplified. In the method in 1) above also, a photo-acid generator is added to a liquid crystal composition containing a polymerizable liquid crystal compound, and the similar compounds can be exemplified. In the method in 2), a photo-acid generator is not added to a liquid crystal composition containing a polymerizable liquid crystal compound, but is used as an organic solvent containing a photo-acid generator, and the similar compounds can be exemplified.

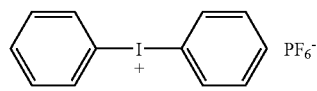
(1)

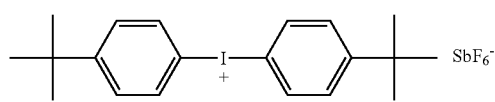
(2)

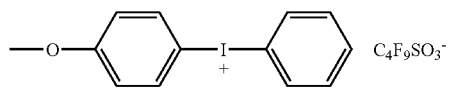
(3)

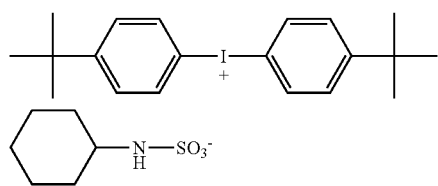
(4)

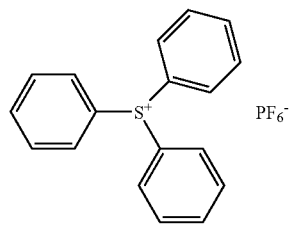
(5)

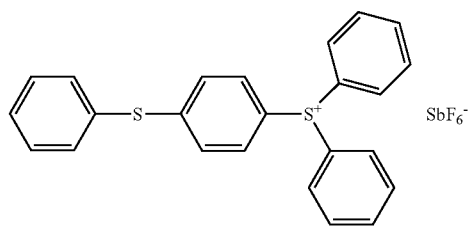
(6)

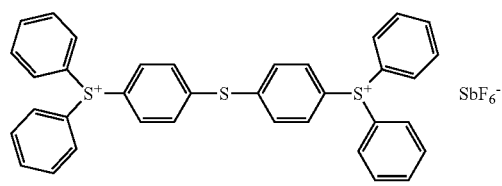
(7)

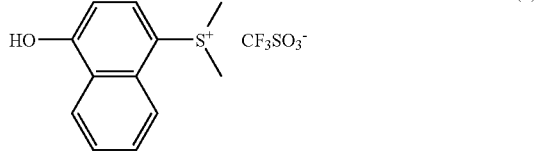
(8)

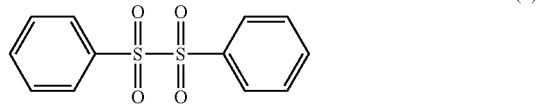
(9)

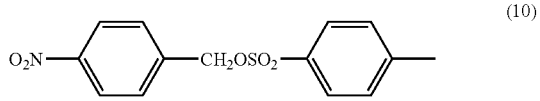
(10)

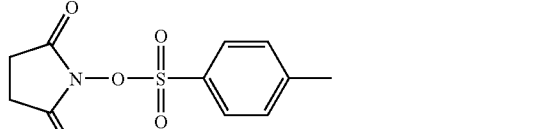
(11)

(12)

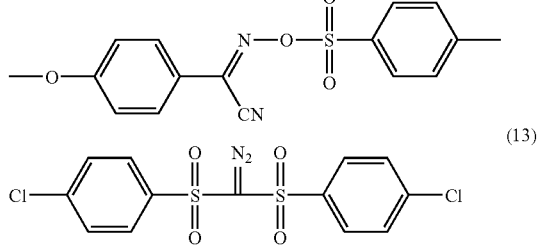
(13)

In polymerizing a polymerizable liquid crystal compound, it can be copolymerized with other monomers. Other monomers are not especially restricted so long as they have radical polymerizability or cationic polymerizability. Any monomer compositions showing a liquid crystal property can be used. For increasing an orientation property, monomers having a mesogenic group are preferably used. If necessary, various kinds of sensitizers can be used in combination.

The addition amount of the photo-acid generator differs depending upon the mesogenic group in a polymerizable liquid crystal compound, the structure of a spacer, the equivalent amount of an oxetanyl group, and orientation condition of liquid crystal, but the amount is generally from 100 mass ppm to 20 mass % based on the total amount of the monomers in the liquid crystal composition, preferably from 1,000 mass ppm to 10 mass %, more preferably from 0.2 mass % to 7 mass %, and most preferably from 0.5 mass % to 5 mass %.

When the composition for forming an optically anisotropic layer contains at least one compound represented by any of the following formulae (I) to (III), and a fluorine—containing homopolymer or copolymer using a monomer represented by formula (IV), the molecules of the liquid crystal compound can be horizontally oriented. Incidentally, in the following description, "horizontal orientation" means that, in the case of rod-like liquid crystal, the long axis of the molecule is in parallel to the horizontal plane of a transparent support, and in the case of disc-like liquid crystal, the disc plane of the core of a disc-like liquid crystal compound is in parallel to the horizontal plane of a transparent support, but this is not to require to be strictly parallel, and in the specification of the invention, "horizontal orientation" means the orientation in which the angle of inclination formed with the horizontal plane is less than 10°. The angle of inclination is preferably from 0 to 5°, more preferably from 0 to 3°, still more preferably from 0 to 2°, and most preferably from 0 to 1°.

Formulae (I) to (IV) are described below in order.

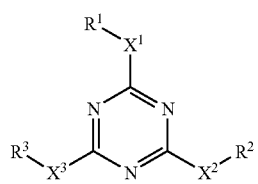

Formula (I)

In Formula (I), $R^1$, $R^2$ and $R^3$ each represents a hydrogen atom or a substituent; and $X^1$, $X^2$ and $X^3$ each represents a single bond or a divalent linking group. The substituents represented by $R^1$, $R^2$ and $R^3$ are preferably a substituted or unsubstituted alkyl group (an unsubstituted alkyl group and a fluorine-substituted alkyl group are more preferred), an aryl group (an aryl group having a fluorine-substituted alkyl group is more preferred), a substituted or unsubstituted amino group, an alkoxyl group, an alkylthio group, and a halogen atom. The divalent linking groups represented by $X^1$, $X^2$ and $X^3$ are preferably an alkylene group, an alkenylene group, a divalent aromatic group, a divalent heterocyclic residue, —CO—, —$NR^a$— ($R^a$ represents an alkyl group having from 1 to 5 carbon atoms or a hydrogen atom), —O—, —S—, —SO—, —$SO_2$—, and a divalent linking group selected from the group consisting of the combinations thereof The divalent linking groups are more preferably divalent linking groups selected from the group consisting of an alkylene group, a phenylene group, —CO—, —$NR^a$—, —O—, —S— and —$SO_2$—, and divalent linking groups of combining at least two of the groups selected from the group. The number of carbon atoms of the alkylene group is preferably from 1 to 12. The number of carbon atoms of the alkenylene group is preferably from 2 to 12. The number of carbon atoms of the divalent aromatic group is preferably from 6 to 10.

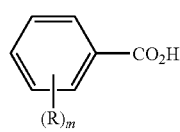

Formula (II)

In formula (II), R represents a substituent; and m represents an integer of from 0 to 5. When m is an integer of 2 or more, a plurality of R's may be the same or different. The preferred substituents represented by R are those exemplified as the preferred substituents represented by $R^1$, $R^2$ and $R^3$. m is preferably an integer of from 1 to 3, and especially preferably 2 or 3.

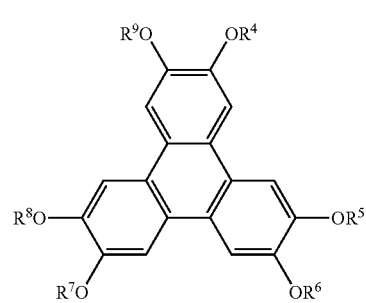

Formula (III)

In formula (III), $R^4$, $R^5$, $R^6$, $R^7$, $R^8$ and $R^9$ each represents a hydrogen atom or a substituent. The preferred substituents represented by $R^4$, R , R6, R7, $R^8$ and $R^9$ are those exemplified as the preferred substituents represented by $R^1$, $R^2$ and $R^3$. As the horizontal orienting agents for use in the invention, the compounds disclosed in JP-A-2005-99248, paragraphs [0092] to [0096] can be used, and the synthesizing methods of these compounds are also disclosed therein.

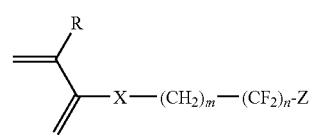

Formula (IV)

In formula (IV), R represents a hydrogen atom or a methyl group; X represents an oxygen atom or a sulfur atom; Z represents a hydrogen atom or a fluorine atom; m represents an integer of from 1 to 6; and n represents an integer of from 1 to 12. As the polymer for improving unevenness in coating, besides the fluorine-containing polymer containing the compound represented by formula (4), the compounds disclosed in JP-A-2005-206638 and JP-A-2006-91205 can also be used as the horizontal orienting agent, and the synthesizing methods of these compounds are also disclosed therein.

The addition amount of the horizontal orienting agent is preferably from 0.01 to 20 mass % of the mass of the liquid crystal compound, more preferably from 0.01 to 10 mass %, and especially preferably from 0.02 to 1 mass %. The compounds represented by any of formulae (I) to (IV) may be used alone, or two or more compounds may be used in combination. The above description of the optically anisotropic layer is also applicable to methods other than the method in item 3) (a manufacturing method of a film having pattern-like phase difference including heating process).

Orientation Layer:

As described above, an orientation layer may be used in forming an optically anisotropic layer. An optically anisotropic layer is generally provided on a transparent support or on an undercoat layer coated on a transparent support. An orientation layer functions to regulate the orientation direction of the liquid crystal compound provided thereon. An orientation layer can be used so long as the layer is capable of giving an orientation property to an optically anisotropic layer. As preferred examples of orientation layers, a layer rubbing-treated with an organic compound (preferably a polymer), a layer obtained by oblique deposition with an inorganic compound, and a layer having micro grooves, further built-in films formed by Langmuir-Blodgett's technique (LB films) such as co-tricosanoic acid, dioctadecylmethylammonium chloride and methyl stearate, and layers obtained by orientation of dielectric substances by the provision of a magnetic field or electric field can be exemplified.

As the examples of the organic compounds for an orientation layer, polymers, e.g., polymethyl methacrylate, acrylic acid/methacrylic acid copolymer, styrene/maleinimide copolymer, polyvinyl alcohol, poly(N-methylolacrylamide), styrene/vinyltoluene copolymer, chlorosulfonated polyethylene, nitrocellulose, polyvinyl chloride, chlorinated polyolefin, polyester, polyimide, vinyl acetate/vinyl chloride copolymer, ethylene/vinyl acetate copolymer, carboxymethyl cellulose, polyethylene, polypropylene, and polycarbonate, and a compound, e.g., a silane coupling agent can be exemplified. As the examples of preferred polymers, polymers of polyimide, polystyrene, styrene derivatives, gelatin, polyvinyl alcohol, and alkyl-modified polyvinyl alcohol having an alkyl group (preferably having 6 or more carbon atoms) can be exemplified.

It is preferred to use in the formation of an orientation layer. The kinds of polymers usable for this purpose can be determined in accordance with the orientation of a liquid crystal compound (in particular, an average angle of inclination). For example, for the purpose of horizontal orientation of a liquid crystal compound, polymers not reducing the surface energy of an orientation layer (generally used polymers for orientation) are used. With respect to the specific kinds of polymers, descriptions are found in various literatures in connection with liquid crystal cells and compensatory sheets. For example, polyvinyl alcohol, modified polyvinyl alcohol, copolymers with polyacrylic acids or polyacrylic esters, polyvinyl pyrrolidone, cellulose or modified cellulose are preferably used. Materials for an orientation layer may have a functional group capable of reaction with the reactive group of a liquid crystal compound. The reactive group can be introduced by the introduction of a repeating unit having a reactive group on a side chain, or can be introduced as a substituent of a cyclic group. It is further preferred to use an orientation layer capable of forming a chemical bond with a liquid crystal compound at interface. Such orientation layers are disclosed in JP-A-9-152509, and modified polyvinyl alcohols obtained by introducing an acryl group into the side chain with acid chloride and Karenz MOI (manufactured by Showa Denko K.K.) are particularly preferred. The thickness of an orientation layer is preferably from 0.0 1 to 5 µm, and more preferably from 0.05 to 2 µm. An orientation layer may have a function of an oxygen-excluding layer.

A polyimide film (preferably fluorine atom-containing polyimide) that is widely used as the orientation layer of LCD is also preferred as the organic orientation layer. This layer can be obtained by coating polyamic acid (e.g., LQ/LX series manufactured by Hitachi Chemical Co., Ltd., and SE series manufactured by Nissan Chemical Industries, Ltd.) on a support surface, baking at 100 to 300° C. for 0.5 to 1 hour, and then rubbing.

A treating method widely adopted as the liquid crystal orientation treatment process of LCD can be used in the rubbing treatment. That is, a method to obtain orientation by rubbing the surface of an orientation layer with paper, gauze, felt, rubber, nylon or polyester fiber can be used. The method is generally carried out by using cloth averagely flocked with fibers uniform in length and thickness and performing rubbing several times.

As the deposition materials of the inorganic oblique deposition film, metal oxides, e.g., $SiO_2$ as representative, $TiO_2$, $ZnO_2$, etc., fluoride, e.g., $MgF_2$, etc., and metals, e.g., Au, Al, etc., are exemplified. Metal oxides are not limited to the above examples, and other metal oxides can also be used as the materials for oblique deposition if they have high dielectric constant. An inorganic oblique deposition film can be formed with a depositing apparatus. An inorganic oblique deposition film can be formed by fixing a film (support) and depositing, or by moving a long size film and continuously depositing.

Adhesive Layer for Transfer:

A transfer material preferably has an adhesive layer for transfer. The adhesive layers for transfer are not especially restricted so long as they are transparent, not colored, and have a sufficient transferring property. Adhesive layers with adhesives, and in particular, a photosensitive resin layer, a pressure-sensitive resin layer and a heat-sensitive resin layer are exemplified, but in view of baking resistance that is required of a functional substrate, a photosensitive resin layer and a heat-sensitive resin layer are preferred. As the adhesives, those excellent in optical transparency and showing appropriate wettability, and sticking characteristics such as a coagulating property and an adhering property are preferably used. As the specific examples, adhesives manufactured with polymers such as acrylic polymers, silicone polymers, polyester, polyurethane, polyether, synthetic rubbers, etc., as arbitrary base polymers are exemplified. The sticking characteristics of the adhesive layer can be appropriately controlled by conventional methods of adjusting the degree of crosslinking and molecular weight by the composition and molecular weight of the base polymer forming the adhesive layer, the way of crosslinking, the content of crosslinking functional groups, and the compounding proportion of the crosslinking agent.

Pressure-sensitive resin layers are not particularly restricted so long as they can reveal an adhesive property by applying pressure, and various adhesives, e.g., rubber, acrylic, vinyl ether, and silicone can be used as the pressure-sensitive adhesive. As the forms of manufacturing stage and coating stage of adhesives, solvent type adhesives, non-aqueous emulsion type adhesives, aqueous emulsion type adhesives, water-soluble type adhesives, hot-melt type adhesives, liquid curable type adhesives, delayed tack type adhesives, etc., can be used. Rubber adhesives are described in *Shin Kobunshi Bunko* 13 "*Nenchaku Gijutsu*" (*New Polymer Library* 13, "*Technique of Adhesion*"), p. 41, Kobunshi Kankokai (1987). Vinyl ether adhesives include adhesives comprising alkyl vinyl ether polymerization product having from 2 to 4 carbon atoms as the main agent, and vinyl chloride/vinyl acetate copolymers, vinyl acetate copolymers, polyvinyl butyral, etc., mixed with plasticizers. As the silicone adhesives, those prepared by using rubber-like siloxane for giving a film-forming property and condensation force to the film, and resinous siloxane for giving adhesion and stickiness can be used.

Heat-sensitive resin layers are not especially limited so long as they can reveal an adhesive property by applying heat, and heat fusion compounds and thermoplastic resins can be exemplified as heat-sensitive adhesives. As the heat fusion compounds, low molecular weight products of thermoplastic resins, e.g., polystyrene resin, acrylic resin, styrene-acryl resin, polyester resin, polyurethane resin, etc., vegetable waxes, e.g., carnauba wax, Japan wax, candelilla wax, rice wax, auricury wax, etc., animal waxes, e.g., bees wax, insect wax, shellac, whale wax, etc., petroleum waxes, e.g., paraffin wax, microcrystalline wax, polyethylene wax, Fischer-Tropsch wax, ester wax, oxide wax, etc., and mineral waxes, e.g., montan wax, ozokerite, ceresin wax, etc., can be exemplified. Other than these compounds, rosin derivatives, e.g., rosin, hydrogenated rosin, polymerized rosin, rosin-modified glycerin, rosin-modified maleic acid resin, rosin-modified polyester resin, rosin-modified phenol resin, ester gum, etc., phenol resin, terpene resin, ketone resin, cyclopentadiene resin, aromatic hydrocarbon resin, aliphatic hydrocarbon resin, alicyclic hydrocarbon resin, etc., can be exemplified.

These heat fusion compounds have a molecular weight of generally 10,000 or less, especially preferably 5,000 or less, and a melting point or softening point of preferably from 50 to 150° C. These heat fusion compounds may be used alone, or two or more kinds may be used in combination. Further, as the thermosetting resins, e.g., ethylene copolymers, polyamide resins, polyester resins, polyurethane resins, polyolefin resins, acryl resins, cellulose resins, etc., can be exemplified. Of these resins, ethylene copolymers are especially preferably used. The photosensitive resin layer is not particularly restricted so long as it can reveal an adhesive property upon light irradiation.

Other Layers:

It is preferred to form a mechanical characteristic controlling layer between a support and an optically anisotropic layer for the purpose of controlling mechanical characteristics and irregularity following up properties. As the mechanical characteristic controlling layer, those showing flexible elasticity, capable of softening by heat, and showing flowability by heat are preferred, and a thermoplastic resin layer is especially preferred. As the components for use in the thermoplastic resin layer, the organic polymer materials as disclosed in JP-A-5-72724 are preferred, and they are especially preferably selected from the organic polymer materials having a softening point of about 80° C or less measured by Vicat method (specifically, polymer softening point measuring method by American Society for Testing Materials, ASTM D1235). As the specific examples, organic polymers, e.g., polyolefins such as polyethylene, polypropylene, etc., ethylene copolymers such as ethylene and vinyl acetate or saponification product thereof, ethylene and acrylic ester or saponification product thereof, polyvinyl chloride, vinyl chloride copolymers such as vinyl chloride and vinyl acetate or saponification product thereof, polyvinylidene chloride, vinylidene chloride copolymer, polystyrene, styrene copolymers such as styrene and (meth)acrylic ester or saponification product thereof, polyvinyltoluene, vinyltoluene copolymers such as vinyltoluene and (meth)acrylic ester or saponification product thereof, poly(meth)acrylic ester, (meth)acrylic ester copolymers such as butyl (meth)acrylate and vinyl acetate, and polyamide resins such as vinyl acetate copolymer nylon, copolymer nylon, N-alkoxymethylated nylon, and N-dimethyl-aminated nylon can be exemplified.

In transfer materials, it is preferred to provide an intermediate layer for the purpose of preventing the components from being mixed in coating a plurality of coating layers and during preservation after coating. As the intermediate layers, an oxygen-excluding layer having an oxygen-excluding function disclosed in JP-A-5-72724 as "separating layer", and the orientation layer for forming optically anisotropy are preferably used. An especially preferred layer of these layers is a layer formed of one or a mixture of a plurality of polyvinyl alcohol or polyvinyl pyrrolidone and modification products thereof Such a layer can also serve as the thermoplastic resin layer, oxygen-excluding layer and orientation layer.

It is preferred to provide a thin protective film on the resin layer for protecting the layer from soiling and damage in preservation. The protective film may consist of the same or analogous materials to the dummy support, but it has to be easily peeled off the resin layer. For example, silicon paper, and polyolefin or polytetrafluoroethylene sheet are preferred as the materials of the protective film.

Each of the optically anisotropic layer, photosensitive resin layer, adhesive layer for transfer, and the orientation layer, thermoplastic resin layer and intermediate layer provided according to necessity can be formed by coating according to dip coating, air knife coating, curtain coating, roller coating, wire bar coating, gravure coating, and extrusion coating (U.S. Pat. No. 2,681,294) methods. Two or more layers may be coated simultaneously. Simultaneous coating methods are described in U.S. Pat. Nos. 2,761,791, 2,941,898, 3,508,947, 3,526,528, and Yuji Harasaki, *Coating Kogaku* (*Coating Engineering*), p. 253, Asakura Shoten (1973).

Coating Methods an Optically Anisotropic Layer on a Substrate:

In the manufacturing method of a functional substrate, an optically anisotropic layer can be formed by the coating of a composition for manufacturing an optically anisotropic layer on a substrate. However, it is possible to decrease the number of manufacturing processes in the manufacture of a functional substrate having a photosensitive layer for forming difference in level by the formation with a transfer material.

Transferring Method of a Transfer Material to a Substrate:

Transferring method of a transfer material to a substrate is not especially restricted, so long as the method is capable of transferring the optically anisotropic layer onto the substrate. For example, a transfer material formed in a film-like form can be stuck on a substrate by pressure bonding or heat bonding with a roller or plate heated and/or pressure applied by using a laminator with the transfer adhesive layer side facing the surface side of the substrate. Specifically, the laminators and lamination methods disclosed in JP-A-7-110575, JP-A-11-77942, JP-A-2000-334836, and JP-A-2002-148794 are exemplified. In the point of low contamination of foreign matters, the method disclosed in JP-A-7-110575 is preferably used. After that, the support may be peeled off, and other layer, e.g., an electrode layer and the like, may be formed on the surface of the optically anisotropic layer bared by peeling off.

Photo-radical generators for use in an organic solvent containing a photo-radical generator are not especially restricted and any compounds can be used so long as they can generate a radical upon irradiation with light. The following compounds are exemplified as representatives. Preferred compounds are 2-trichloromethyl-5-(p-styrylmethyl)-1,3,4-oxadiazole and 2,4-bis(trichloromethyl)-6-[4-(N,N-diethoxycarbonylmethyl)-3-bromophenyl]-s-triazine. In the above methods 1) and 2), a photo-radical generator is added to a liquid crystal composition containing a polymerizable liquid crystal compound, and the similar compounds can be exemplified. The addition amount of a photo-radical generator to a liquid crystal composition differs depending upon the mesogenic group in a polymerizable liquid crystal compound, the structure of a spacer, the equivalent amount of an oxetanyl group, and orientation condition of liquid crystal, but the amount is generally from 100 mass ppm to 20 mass % based on the total amount of the monomers in the liquid crystal composition, preferably from 1,000 mass ppm to 10 mass %, more preferably from 0.2 mass % to 7 mass %, and most preferably from 0.5 mass % to 5 mass %.

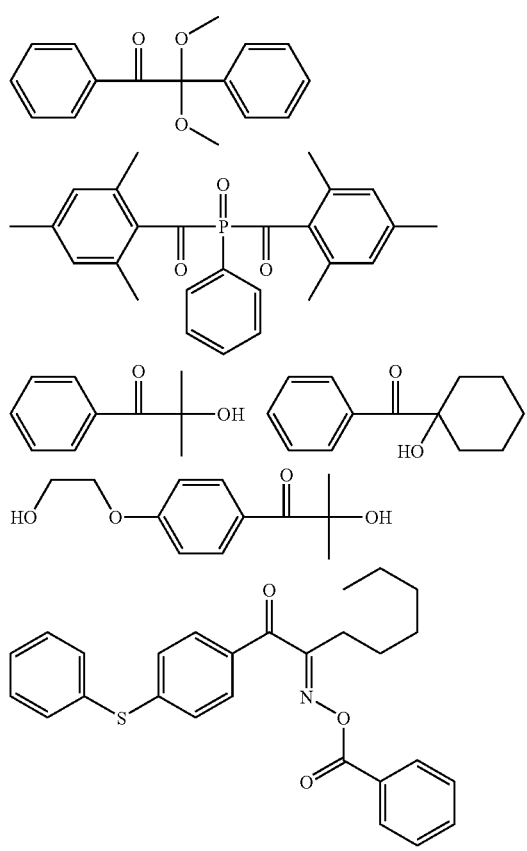
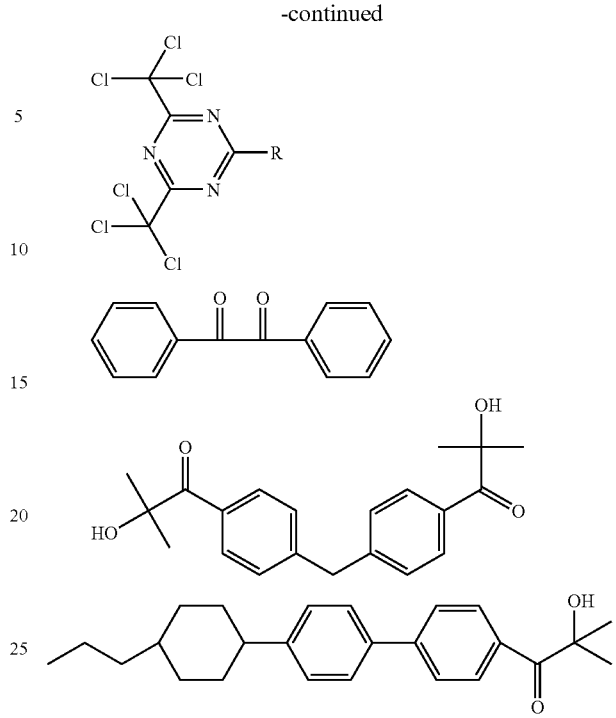
R = H, alkyl
Embodiment
The invention will be described more specifically with reference to examples, but the invention should not be construed as being restricted thereto.
EXAMPLE 1
Compound 11, an acryloyl compound having an oxetanyl group, is synthesized in accordance with the following scheme 1.
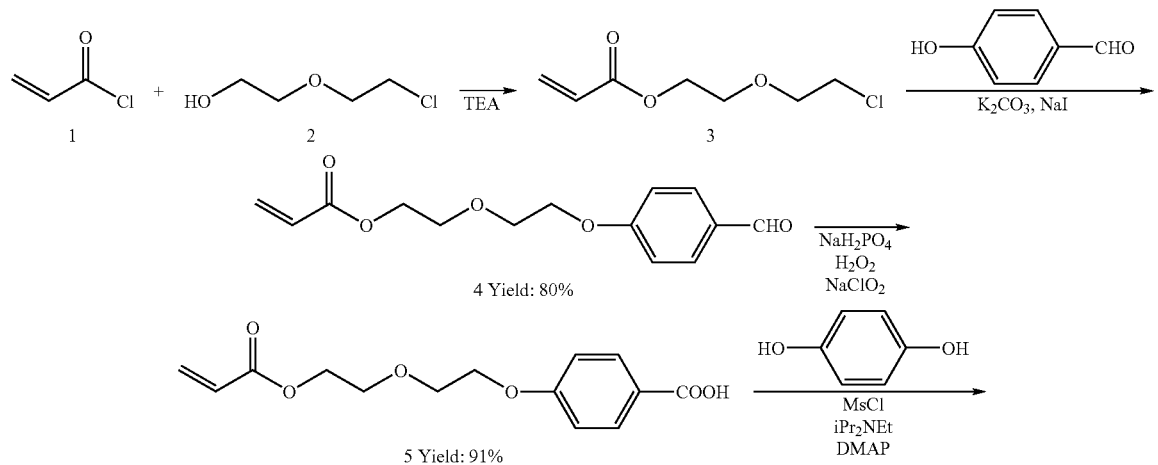

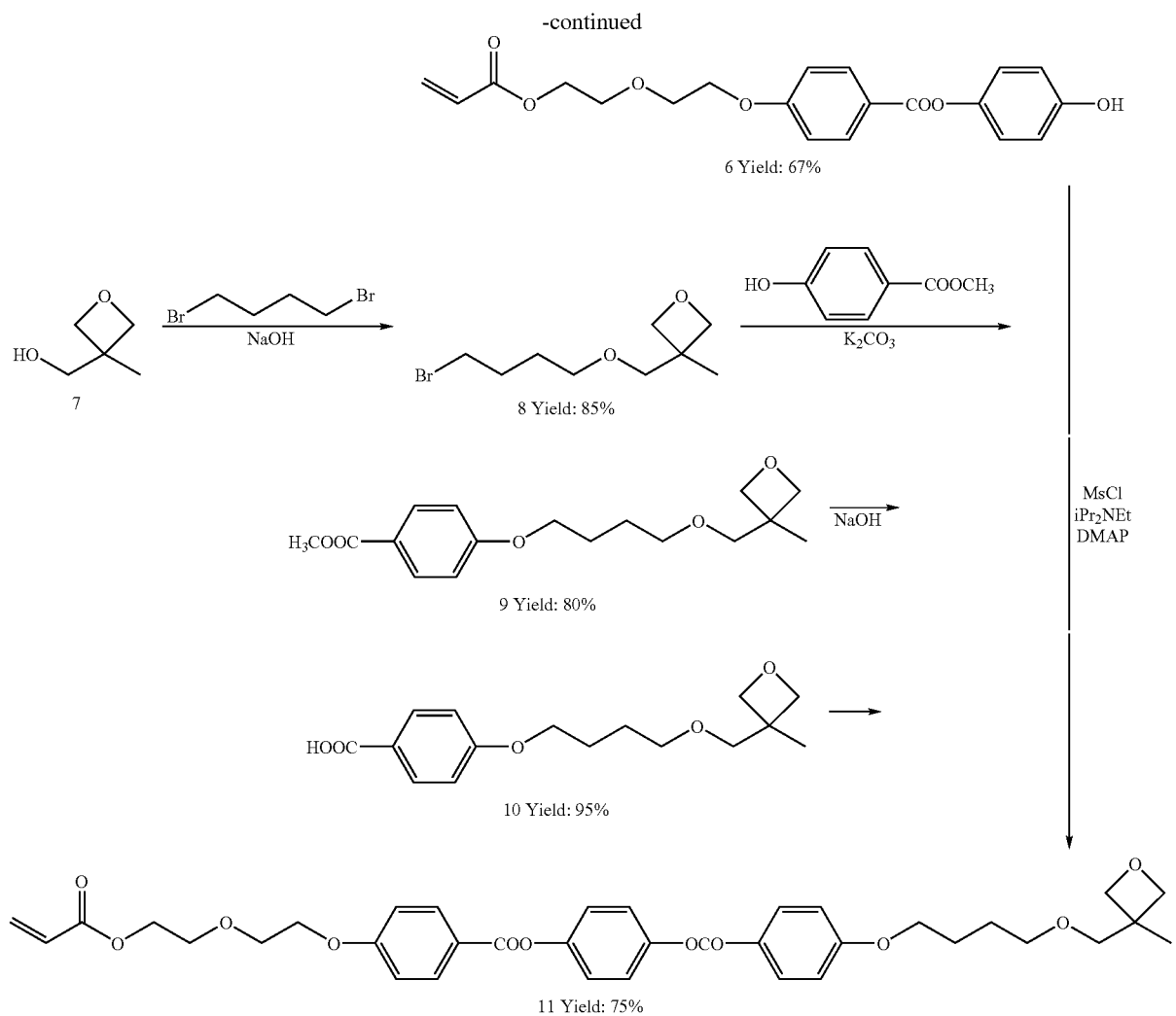

(1-1) A three-neck flask having a capacity of 2 liters is charged with 100 g of compound 2, 86 g of triethylamine (TEA), and 1,000 ml of tetrahydrofuran, and the reaction mixture is cooled at 0° C. Compound 1 (76 g) is dropped to the reaction mixture and the temperature is raised to room temperature, followed by reaction for 30 minutes. After being diluted with 300 ml of ethyl acetate, the reaction solution is washed with water. The reaction product is refined with column chromatography to obtain 70 g of compound 3.

(1-2) A three-neck flask having a capacity of 1,000 ml is charged with 25 g of compound 3, 16 g of 4-hydroxybenzaldehyde, 225 ml of N,N-dimethylacetamide, 55 g of potassium carbonate, 0.5 g of sodium iodide, and 0.1 ml of nitrobenzene. The reaction mixture is subjected to reaction in an oil bath at 100° C. under a nitrogen atmosphere for 4 hours. After being diluted with 200 ml of ethyl acetate, the reaction solution is washed with dilute hydrochloric acid, and further with water. The reaction product is refined with column chromatography to obtain 25 g of compound 4.

(1-3) A three-neck flask having a capacity of 500 ml is charged with 25 g of compound 4, 195 ml of acetonitrile, 20 g of a 17 wt % sodium dihydrogenphosphate aqueous solution, and 23 g of 31 wt % aqueous hydrogen peroxide, and the reaction mixture is stirred at room temperature. To the reaction solution is dropped 110 g of a 14 wt % sodium chlorite aqueous solution. After being reacted at 50° C. for 4 hours, the reaction solution is added to 1,000 ml of distilled water to obtain a precipitate. The precipitate is washed with 50 ml of acetonitrile to obtain 23 g of compound 5.

(1-4) A three-neck flask having a capacity of 500 ml is charged with 13 g of compound 5, 200 ml of tetrahydrofuran, and 5.8 g of methanesulfonyl chloride, and the reaction mixture is cooled at 0° C. Diisopropylethylamine (6.6 g) is dropped to the reaction mixture and the temperature is raised to room temperature, followed by reaction for 30 minutes. After that, 20.4 g of hydroquinone is added thereto and again cooled to 0° C. Diisopropylethylamine (6.6 g) and 0.6 g of N,N-dimethyl-aminopyridine are added to the reaction solution, and the temperature is raised to room temperature, followed by reaction for 30 minutes. After being diluted with 100 ml of ethyl acetate, the reaction solution is washed with water. The reaction product is refined with column chromatography to obtain 8.6 g of compound 6.

(1-5) A three-neck flask having a capacity of 2 liters is charged with 50 g of compound 7, 8.2 g of tetrabutylammonium bromide, 400 ml of hexane, 640 g of a 50 wt % sodium hydroxide aqueous solution, and 317 g of 1,4- dibromobutane. The reaction mixture is reacted at room temperature for 30 minutes, and for 4 hours while refluxing. After the reaction solution is washed with water, the solvent is removed. The reaction product is refined by distillation to obtain 87 g of compound 8.

(1-6) A three-neck flask having a capacity of 500 ml is charged with 20 g of compound 8, 200 ml of N,N-dimethylacetamide, 12.8 g of methyl 4-hydroxybenzoate, and 35 g of potassium carbonate, and the reaction mixture is reacted at 150° C. for 8 hours. After being diluted with 200 ml of ethyl acetate, the reaction solution is washed with water to obtain 25 g of compound 9.

(1-7) A three-neck flask having a capacity of 500 ml is charged with 25 g of compound 8, 100 ml of isopropyl alcohol, 100 ml of distilled water, and 8 g of sodium hydroxide. The reaction mixture is subjected to reaction in an oil bath at 110° C. for 4 hours. After being diluted with 200 ml of ethyl acetate, the reaction solution is washed with dilute hydrochloric acid, and further with water to obtain 18 g of compound 10.

(1-8) A three-neck flask having a capacity of 100 ml is charged with 3.4 g of compound 10, 18 ml of tetrahydrofuran, and 1.4 g of methanesulfonyl chloride, and the reaction mixture is cooled at 0° C. Diisopropylethylamine (1.6 g) is dropped to the reaction mixture and the temperature is raised to room temperature, followed by reaction for 30 minutes. After that, 4.7 g of compound 6 is added thereto and again cooled to 0° C. Diisopropylethylamine (1.6 g) and 0.3 g of N,N-dimethyl-aminopyridine are added to the reaction solution, and the temperature is raised to room temperature, followed by reaction for 30 minutes. After being diluted with 100 ml of ethyl acetate, the reaction solution is washed with water. The reaction product is refined with column chromatography, and further recrystallized with methanol to obtain 4.7 g of compound 11.

$^1$H-NMR of compound 11 (CDCl$_3$, ppm): 1.35, 1.7-2.1, 3.4-4.6, 5.8-6.6, 6.9-7.1, 7.2-7.3, 8.1-8.2

The nematic temperature range of the obtained compound is from 66 to 112° C.

EXAMPLE 2

Compound 17, an acryloyl compound having an oxetanyl group, is synthesized in accordance with the following scheme 2.

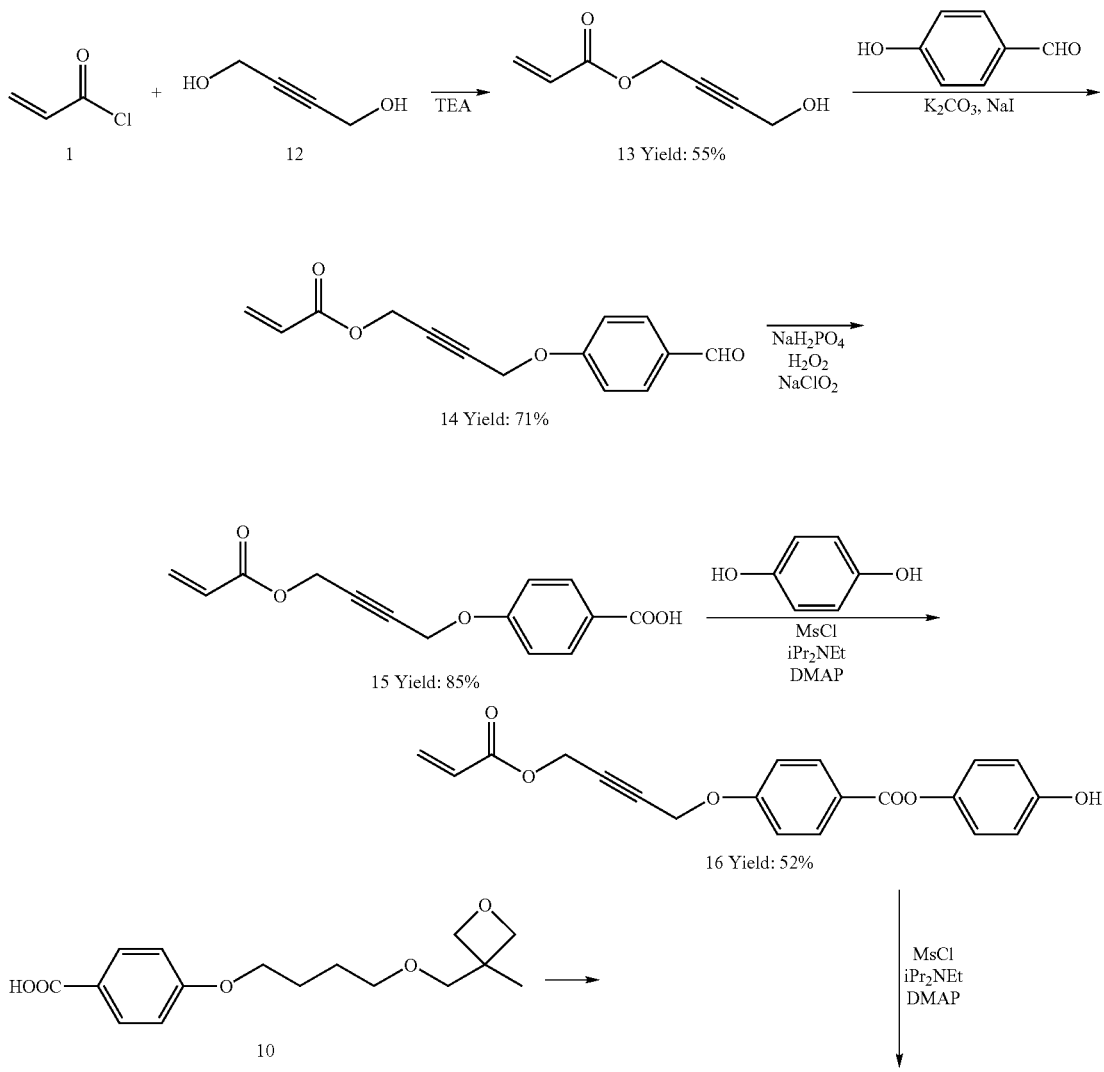

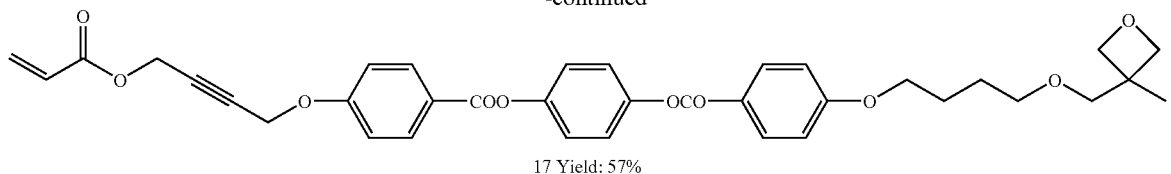

17 Yield: 57%

(2-1) Compound 13 is obtained according to the same operation as (1-1).

(2-2) Compound 14 is obtained according to the same operation as (1-2).

(2-3) Compound 15 is obtained according to the same operation as (1-3).

(2-4) Compound 16 is obtained according to the same operation as (1-4).

(2-5) Compound 17 is obtained according to the same operation as (1-8).
$^1$H-NMR of compound 17 (CDCl$_3$, ppm): 1.35, 1.6-2.1, 2.25, 3.4-3.7, 4.0-5.0, 5.7-6.6, 6.8-7.5, 8.0-8.3

The nematic temperature range of the obtained compound is from 88 to 115° C.

EXAMPLE 3

Compound 23, an acryloyl compound having an oxetanyl group, is synthesized in accordance with the following scheme 3.

Reaction Scheme 3

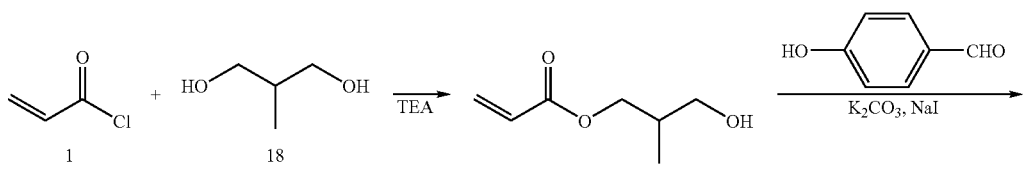

19 Yield: 52%

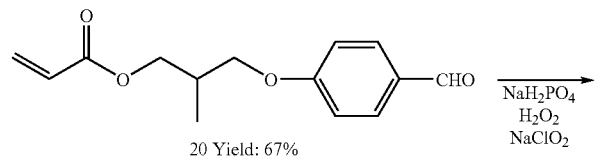

20 Yield: 67%

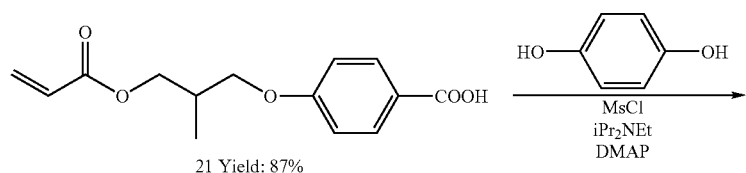

21 Yield: 87%

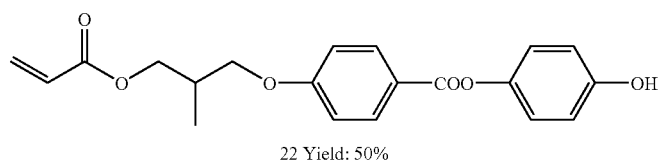

22 Yield: 50%

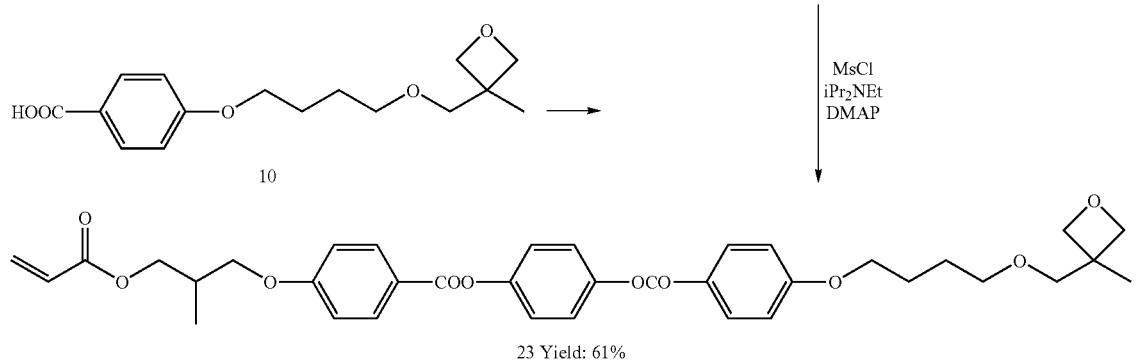

(3-1) Compound 19 is obtained according to the same operation as (1-1).
(3-2) Compound 20 is obtained according to the same operation as (1-2).
(3-3) Compound 21 is obtained according to the same operation as (1-3).
(3-4) Compound 22 is obtained according to the same operation as (1-4).
(3-5) Compound 23 is obtained according to the same operation as (1-8).

$^1$H-NMR of compound 23 (CDCl$_3$, ppm): 1.0-1.4, 1.7-2.1, 2.3-2.6, 3.4-3.7, 3.8-4.6, 5.7-6.6, 6.8-7.5, 8.0-8.3

The nematic temperature range of the obtained compound is from 87 to 106° C.

EXAMPLE 4

Compound 29, an acryloyl compound having an oxetanyl group, is synthesized in accordance with the following scheme 4.

Reaction Scheme 4

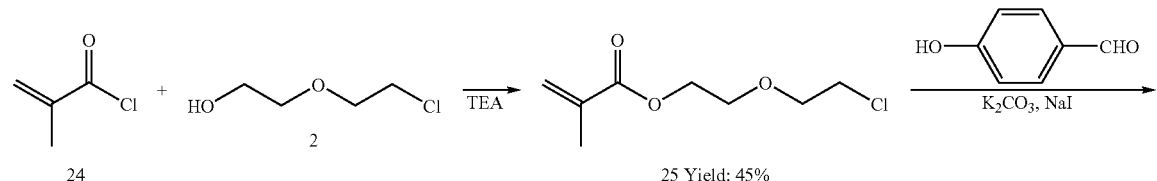

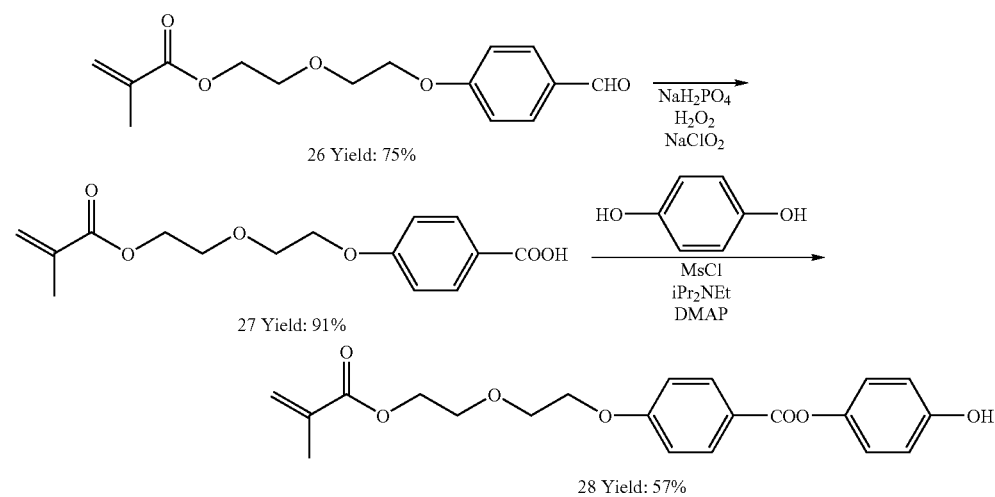

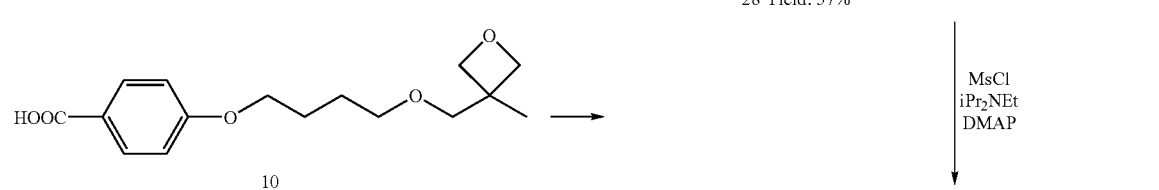

-continued

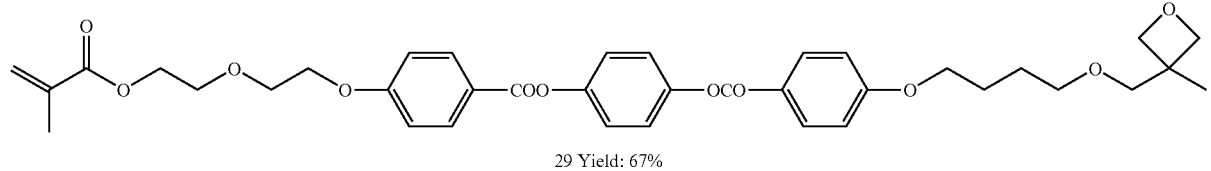

29 Yield: 67%

(4-1) Compound 25 is obtained according to the same operation as (1-1).
(4-2) Compound 26 is obtained according to the same operation as (1-2).
(4-3) Compound 27 is obtained according to the same operation as (1-3).
(4-4) Compound 28 is obtained according to the same operation as (1-4).
(4-5) Compound 29 is obtained according to the same operation as (1-8).

$^1$H-NMR of compound 29 (CDCl$_3$, ppm): 1.35, 1.7-2.1, 3.4-4.6, 5.8-6.6, 6.9-7.1, 7.2-7.3, 8.1-8.2

The nematic temperature range of the obtained compound is from 57 to 108° C.

EXAMPLE 5

Compound 34, an acryloyl compound having an oxetanyl group, is synthesized in accordance with the following scheme 5.

Reaction Scheme 5

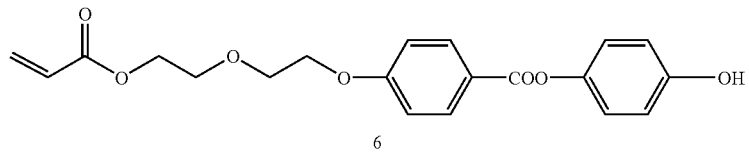

6

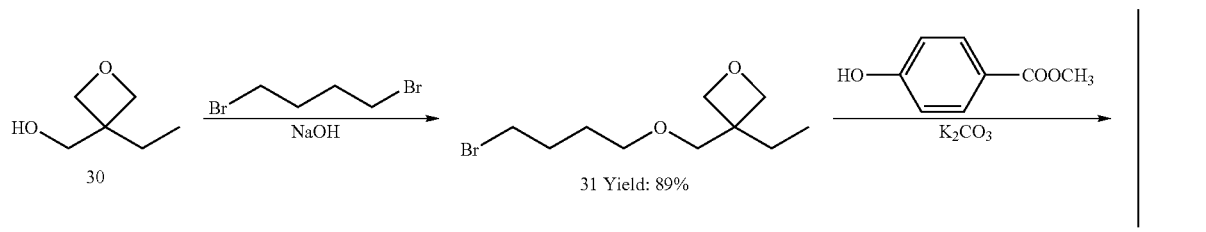

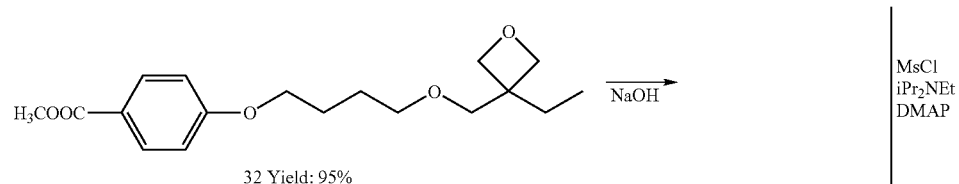

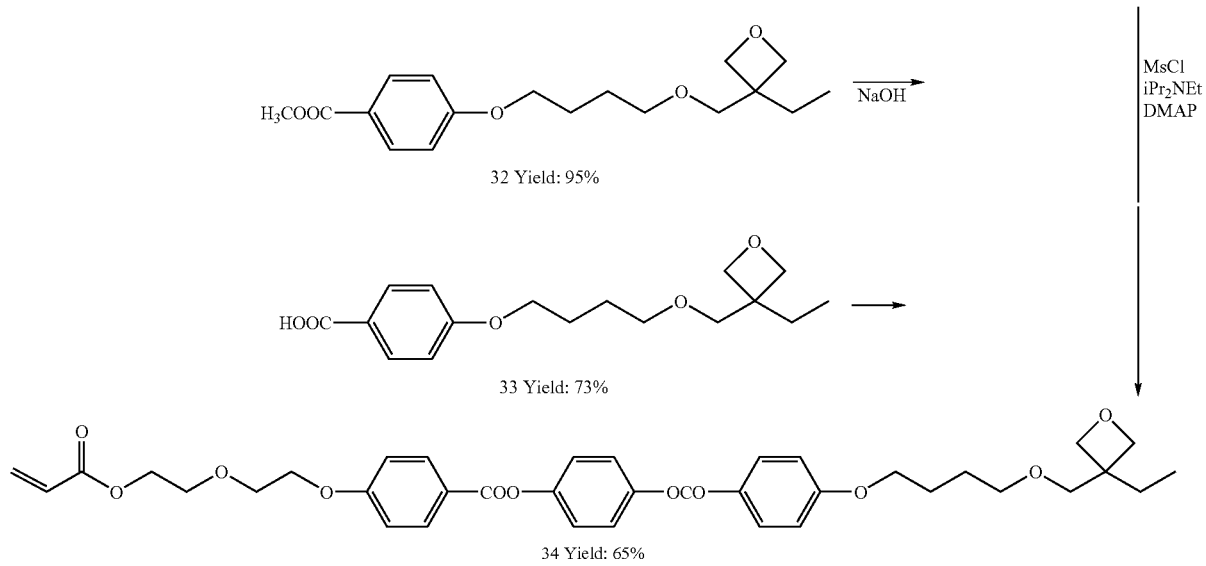

(5-1) Compound 31 is obtained according to the same operation as (1-5).

(5-2) Compound 32 is obtained according to the same operation as (1-6).

(5-3) Compound 33 is obtained according to the same operation as (1-7).

(5-4) Compound 34 is obtained according to the same operation as (1-8).

$^1$H-NMR of compound 34 (CDCl$_3$, ppm): 0.8-1.0, 1.6-2.1, 3.4-3.6, 3.7-4.6, 5.7-6.6, 6.8-7.4, 8.0-8.3

The nematic temperature range of the obtained compound is from 67 to 107° C.

EXAMPLE 6

Compound 35, an acryloyl compound having an oxetanyl group, is synthesized in accordance with the following scheme 6.

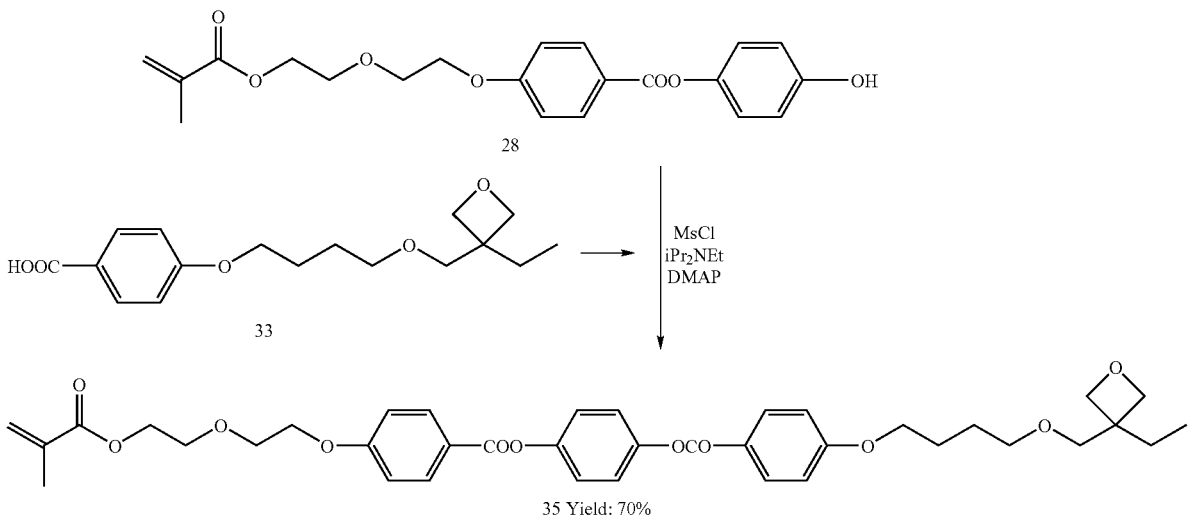

Reaction Scheme 6

(6-1) Compound 35 is obtained according to the same operation as (1-8).

$^1$H-NMR of compound 35 (CDCl$_3$, ppm): 0.7-1.2, 1.5-2.2, 3.3-4.7, 5.5-5.6, 6.1-6.2, 6.8-7.4, 8.0-8.3

COMPARATIVE EXAMPLE 1

Compound 37, an acryloyl compound having an oxetanyl group, is synthesized in accordance with the following scheme 7.

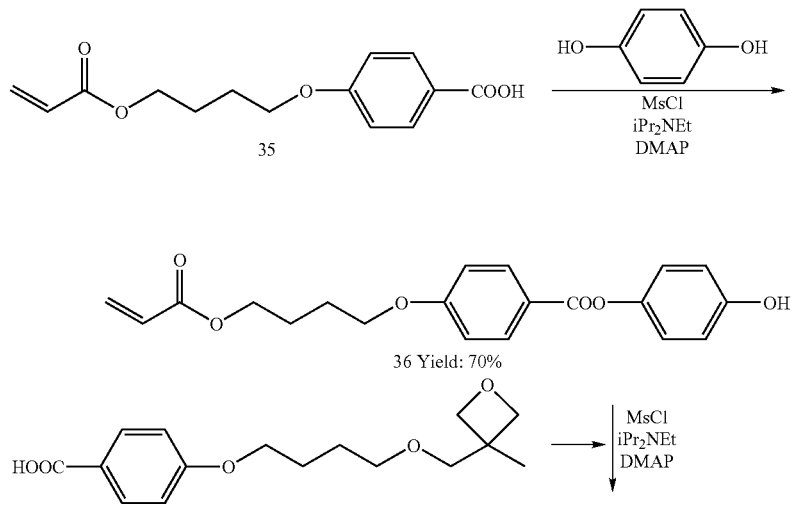

Reaction Scheme 7

-continued

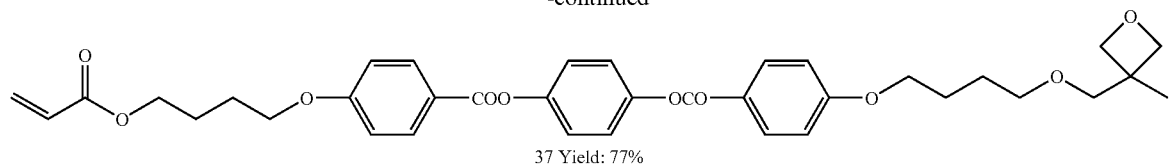
37 Yield: 77%

(7-1) Compound 36 is obtained according to the same operation as (1-4).

(7-2) Compound 37 is obtained according to the same operation as (1-8).

¹H-NMR of compound 37 (CDCl$_3$, ppm): 1.30, 1.70-2.00, 3.4-3.65, 5.75-6.50, 6.85-7.35, 8.05-8.25

The nematic temperature range of the obtained compound is from 89 to 141° C.

COMPARATIVE EXAMPLE 2

Compound 29, an acryloyl compound having an oxetanyl group, is synthesized in accordance with the following scheme 8.

Reaction Scheme 8

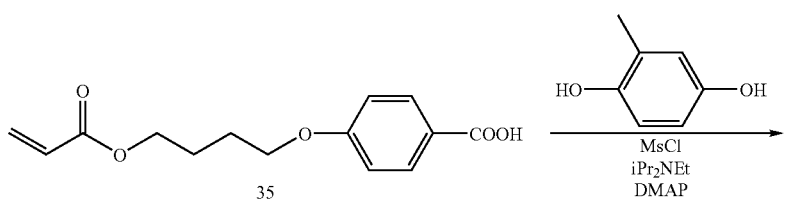

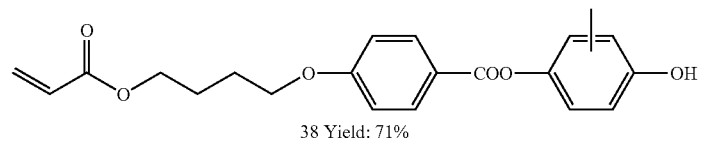
38 Yield: 71%

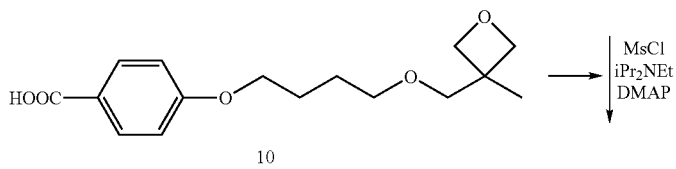

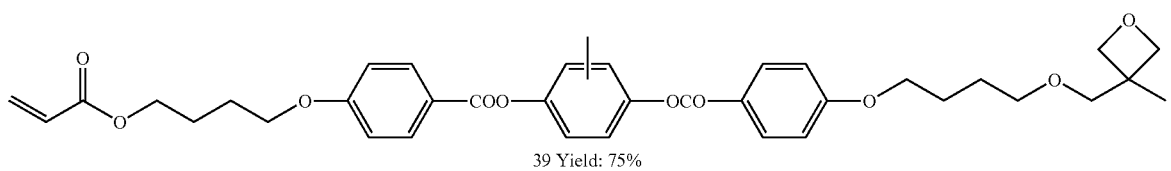
39 Yield: 75%

(8-1) Compound 38 is obtained according to the same operation as (1-4).

(8-2) Compound 39 is obtained according to the same operation as (1-8).

$^1$H-NMR of compound 39 (CDCl$_3$, ppm): 1.35, 1.6-2.1, 2.25, 3.4-3.7, 4.0-4.7, 5.7-6.6, 6.8-7.3, 8.0-8.3

The nematic temperature range of the obtained compound is from 70 to 87° C.

A phase difference film having pattern-like phase difference is formed by the following operation with each of the compounds synthesized in Examples 1 to 6 and Comparative Examples 1 and 2.

A liquid crystal composition comprising the polymerizable liquid crystal compound of the invention (106 parts), 0.11 parts of polymerization inhibitor (Irganox 1076, manufactured by Ciba Specialty Chemicals Inc.), 2.2 parts of photo-polymerization initiator (triarylsulfonium hexafluoroantimonate salt), 0.2 parts of a horizontal orienting agent (LC-1-1), and 105 parts of MEK is coated on a glass substrate having been subjected to rubbing treatment in advance with polyvinyl alcohol (at 2,000 rpm for 20 seconds). The substrate is heated to temperature range until the polymerizable liquid crystal compound takes liquid crystal temperature, the temperature is maintained for 2 minutes, and then irradiated with light of 80 mJ in the atmosphere to cationically polymerize the oxetanyl group (partial progress of radical polymerization is also confirmed by IR). Subsequently, a 5 wt % MEK solution of a photo-radical generator (2-trichloromethyl-5-(p-styryl-methyl)-1,3,4-oxadiazole) is coated on the obtained film (at 2,000 rpm for 20 seconds). After pattern exposure by 80 mJ through a mask in the atmosphere, the substrate is heated at 230° C. for 3 minutes to obtain the substrate having pattern-like phase difference.

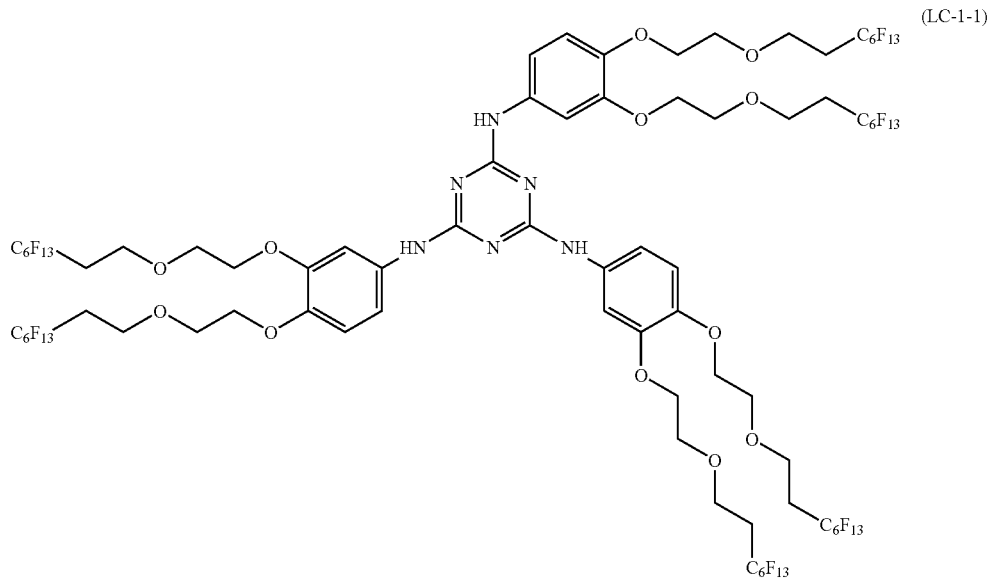

The solubility in MEK (methyl ethyl ketone) of the compound synthesized in each Example, retardation (Re) in the unexposed part and exposed part of the phase difference film, and the presence of haze, streak/unevenness are shown in Table 1 below. Each characteristic is evaluated according to the following procedure.

Solubility in MEK:

MEK solution prepared in each concentration is stirred at 20° C. for 1 hour, and whether the compound is dissolved or not is confirmed. In Table 1, solubility of 33 wt % or more means that the dissolution of compound until 33 wt % is confirmed, less than 20 wt % means that it is confirmed that the compound does not dissolve at 20 wt %, and as to 54 wt %, measurement is performed according to the following procedure.

(1): By using three kinds of solutions whose concentrations are known, calibration curve is drawn with HPLC.
(2): A saturated MEK solution (60 wt %) is prepared and allowed to stand at 20° C. overnight.
(3): The supernatant is collected and measured with HPLC.
(4): Saturated concentration is computed from the calibration curve made in (1).

Measurement of Retardation (Re):

An Re value is measured with a phase difference meter (KOBRA 21DH, manufactured by Oji Scientific Instruments).

Haze:

Each of the exposed samples in Examples and Comparative Examples is subjected to heat developing treatment, and the haze of the exposed part of each sample is measured with Model NDH300A (manufactured by Nippon Denshoku Industries Co., Ltd.).

Streak/Unevenness:

The presence of a streak and unevenness is confirmed by visual observation.

TABLE 1

| Example No. | Structure |
|---|---|
| Example 1 | (structure) |
| Example 2 | (structure) |
| Example 3 | (structure) |
| Example 4 | (structure) |
| Example 5 | (structure) |
| Example 6 | (structure) |
| Comparative Example 1 | (structure) |
| Comparative Example 2 | (structure) |

| Example No. | Solubility in MEK (wt %) | Re in Unexposed Part (nm) | Re in Exposed Part (nm) | Haze | Streak or Uneveness |
|---|---|---|---|---|---|
| Example 1 | 54 | 1.5 | 298 | 0.05 | None |
| Example 2 | 33 or more | 2.5 | 278 | 1.53 | None |
| Example 3 | 33 or more | 2.7 | 285 | 1.65 | None |
| Example 4 | 33 or more | 0.5 | 301 | 1.22 | None |

TABLE 1-continued

| | | | | | |
|---|---|---|---|---|---|
| Example 5 | 33 or more | 2.2 | 293 | 1.57 | None |
| Example 6 | 33 or more | 0.3 | 305 | 0.02 | None |
| Comparative Example 1 | Less than 20 | 130 | 353 | 5.78 | Unevenness is present. |
| Comparative Example 2 | — | 5.4 | 103 | 7.45 | Streak is present. |

From the results shown in Table 1, it can be confirmed that spacer parts of the compounds of the invention prepared in Examples 1 to 6 are asymmetric, so that they are excellent in solubility in MEK. Further, since the phase difference films of the invention are excellent in heat resistance of pattern exposed parts, retardation of the pattern exposed parts is great. Further, appropriate motility can be secured when spacer parts are asymmetric, it is confirmed that the phase difference films of the invention are small in residual retardation of the pattern unexposed part. Further, the phase difference films of the invention are also excellent in an orientation property, so that haze is small. Contrary to this, the spacer parts of the compounds in Comparative Examples 1 and 2 are not substituted alkylenes, solubility in MEK is low, so that the phase difference films obtained with these compounds are small in the difference between the retardation of the pattern exposed part and the retardation of the pattern unexposed part, and haze is great.

INDUSTRIAL APPLICABILITY

The polymerizable liquid crystal compound in the invention has very high solubility in an organic solvent (e.g., MEK). Accordingly, when a phase difference film is formed with the polymerizable liquid crystal compound as a monomer, it is possible to form a thin film excellent in surface properties, etc.

The entire disclosure of each and every foreign patent application from which the benefit of foreign priority has been claimed in the present application is incorporated herein by reference, as if fully set forth.

The invention claimed is:
1. A polymerizable liquid crystal compound represented by the following formula (1):

$$P\text{-}Sp^1\text{-}L^1\text{-}M^1\text{-}L^2\text{-}Sp^2\text{-}Ox \quad (1)$$

wherein
P represents a polymerizable group which is a (meth)acryloyloxy group or a (meth)acryloyl group;
one of $Sp^1$ and $Sp^2$ represents an alkylene group containing —O— or —C≡C— in the chain thereof, wherein the alkylene group containing —O— or —C≡C— in the chain thereof is represented by —$(CH_2)_{n1}$—X—$(CH_2)_{n2}$—
wherein
each of n1 and n2 independently represents an integer of from 1 to 4; and
—X— represents —O— or C≡C;
the other of $Sp^1$ and $Sp^2$ represents a straight chain alkylene group;
each of $L^1$ and $L^2$ independently represents a divalent linking group;
$M^1$ represents a mesogenic group having at least one divalent group selected from the group consisting of the following formulae (2-1) to (2-12); and Ox represents a group represented by the following formula (3):

(2-1)

(2-2)

(2-3)

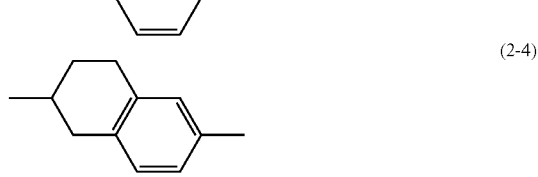
(2-4)

(2-5)

(2-6)

(2-7)

(2-8)

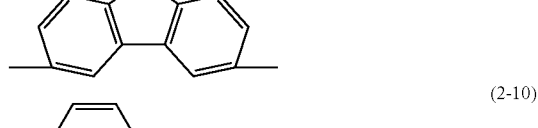
(2-9)

(2-10)

(2-11)

(2-12)

-continued

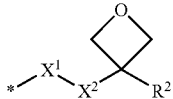 (3)

wherein
R² represents a hydrogen atom, a methyl group or an ethyl group;
X¹ represents —O—, —S—, —OCO— or —COO—;
X² represents a single bond or an alkylene group having from 1 to 4 carbon atoms; and
* is a bonding site to Sp².

2. The polymerizable liquid crystal compound according to claim 1, wherein
Sp² is a straight chain alkylene group.

3. The polymerizable liquid crystal compound according to claim 1, wherein
each of L¹ and L² independently represents a single bond, —O—, —S—, —OCO—, —COO—, —CO—, —CH₂—, —CONH— or —NHCO—.

4. The polymerizable liquid crystal compound according to claim 3,
wherein each of L¹ and L² independently represents —O—.

5. The polymerizable liquid crystal compound according to claim 1, wherein
M¹ is a group represented by the following formula (5):

-Hex¹-Sp³-Hex²-Sp⁴-Hex³- (5)

wherein
each of Hex¹, Hex², and Hex³ independently represents a substituted or unsubstituted 1,4-phenylene group, or a substituted or unsubstituted 1,4-cyclohexylene group; and
each of Sp³ and Sp⁴ independently represents a single bond, —OCO—, —COO—, or an acetylene group.

6. The polymerizable liquid crystal compound according to claim 5,
wherein
one of Sp³ and Sp⁴ represents —COO—; and
the other of Sp³ and Sp⁴ represents —OCO—.

7. The polymerizable liquid crystal compound according to claim 5, wherein
each of Hex¹, Hex², and Hex³ independently represents a substituted or unsubstituted 1,4-phenylene group.

8. The polymerizable liquid crystal compound according to claim 1, wherein
X¹ represents —O—; and
X² represents methylene.

9. A composition containing the polymerizable liquid crystal compound according to claim 1.

10. A phase difference film, which is formed with the composition according to claim 9.

11. The phase difference film according to claim 10, which has pattern-like phase difference.

12. A liquid crystal display, comprising the phase difference film according to claim 10.

* * * * *